United States Patent
Kamdar et al.

(12)

(10) Patent No.: US 12,090,120 B2
(45) Date of Patent: Sep. 17, 2024

(54) FLUID CONTAINER DEVICES, METHODS AND SYSTEMS

(71) Applicant: DEKA Products Limited Partnership, Manchester, NH (US)

(72) Inventors: Akshay R. Kamdar, Zionsville, IN (US); Daniel M. Hartmann, Arlington, MA (US); Gavin M. McKeown, Bedford, MA (US); James A. Davies, Upper Cambourne (GB)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 448 days.

(21) Appl. No.: 17/481,554

(22) Filed: Sep. 22, 2021

(65) Prior Publication Data

US 2022/0000718 A1 Jan. 6, 2022

Related U.S. Application Data

(63) Continuation of application No. 16/431,916, filed on Jun. 5, 2019, now Pat. No. 11,129,772.

(60) Provisional application No. 62/680,901, filed on Jun. 5, 2018.

(51) Int. Cl.
| | |
|---|---|
| *A61J 1/20* | (2006.01) |
| *A61J 1/14* | (2023.01) |
| *A61M 5/162* | (2006.01) |

(52) U.S. Cl.
CPC ............ *A61J 1/2048* (2015.05); *A61J 1/1406* (2013.01); *A61J 1/201* (2015.05); *A61M 5/162* (2013.01)

(58) Field of Classification Search
CPC ........ A61J 1/2048; A61J 1/1406; A61J 1/201; A61M 5/162; A61M 5/14248; A61M 2005/14268; A61M 2039/267
See application file for complete search history.

(56) References Cited

U.S. PATENT DOCUMENTS

| | | | |
|---|---|---|---|
| 4,699,356 A | 10/1987 | Hargrove et al. | |
| 6,892,999 B2 * | 5/2005 | Hall | G01N 1/2035 |
| | | | 251/149.6 |
| 7,455,280 B2 * | 11/2008 | Parrish | F16L 37/0925 |
| | | | 251/149.6 |
| 9,145,983 B2 | 9/2015 | Smith, III | |
| 2014/0052101 A1 | 2/2014 | Stroup | |
| 2017/0143896 A1 | 5/2017 | Lorenzen et al. | |

FOREIGN PATENT DOCUMENTS

WO    WO2012099898 A2    7/2012

* cited by examiner

*Primary Examiner* — Philip R Wiest
*Assistant Examiner* — Matthew Wrubleski
(74) *Attorney, Agent, or Firm* — Mark E. Tetreault

(57) ABSTRACT

A drug container assembly for use with a parenteral drug delivery device is disclosed. The container assembly includes a container configured to hold the medication and an intermediate port connector. The port connector may be fixedly coupled to the container and removably coupled to the delivery device in a convenient, reliable, and sealed manner. In use, the port connector may convey the medication from the container to the delivery device for delivery to the patient.

6 Claims, 29 Drawing Sheets

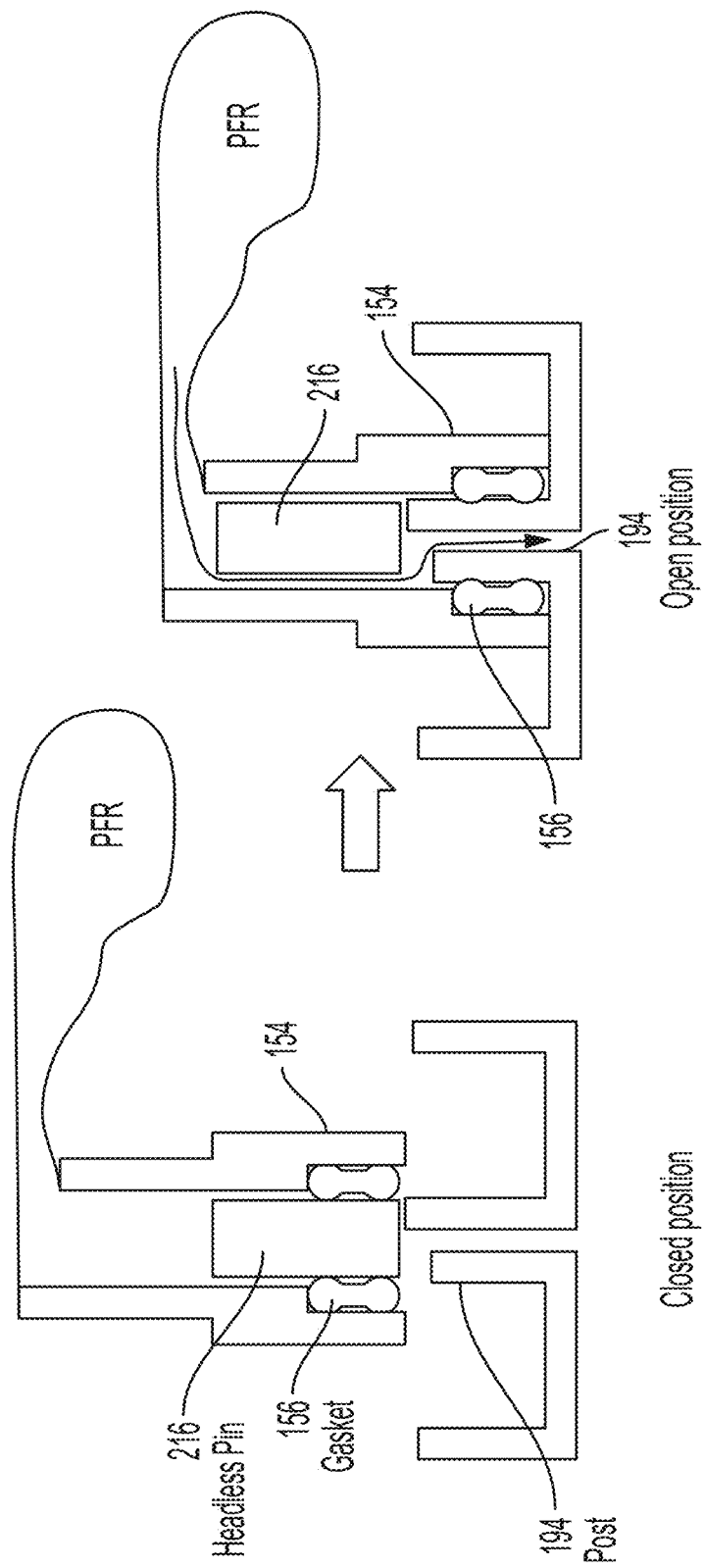

FLUID CONTAINER DEVICES, METHODS AND SYSTEMS

CROSS REFERENCE TO RELATED APPLICATION(S)

The present application is a Continuation Application of U.S. patent application Ser. No. 16/431,916, filed Jun. 5, 2019 and entitled Fluid Container Devices, Methods and Systems, now U.S. Pat. No. 11,129,772, issued Sep. 28, 2021, which claims priority from U.S. Provisional Patent Application Ser. No. 62/680,901, filed Jun. 5, 2018 and entitled Fluid Container Devices, Methods and Systems, which is hereby incorporated herein by reference in its entirety.

TECHNICAL FIELD

The present disclosure relates to medical devices and more particularly, to a fluid container device, method and system.

BACKGROUND INFORMATION

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the user/caregiver manually loading the reservoir with medication, which may be inconvenient, time consuming, and susceptible to user error, drug leakage, and/or contamination.

SUMMARY

In accordance with one aspect of the present invention, a parenteral drug delivery system for delivering medication to a patient. The delivery system includes a container configured to hold the medication, an intermediate port connector, and a delivery device. The port connector may be fixedly coupled to the container and removably coupled to the delivery device in a convenient, reliable, and sealed manner. During a delivery process, the port connector may convey the medication from the container to the delivery device for delivery to the patient.

In accordance with another aspect of the present invention, a container assembly is provided for holding a medication for delivery to a patient via a delivery device. The container assembly includes a container configured to hold the medication and a port connector coupled to the container and having a delivery port with an inlet and an outlet. The delivery port includes a pin, a first seal, and a second seal. The port connector has: a sealed configuration in which the first and second seals are positioned in sealed engagement with the pin to close the delivery port; an intermediate configuration in which the first seal is positioned in sealed engagement with the delivery device and the second seal is positioned in sealed engagement with the pin; and a delivery configuration in which the first seal is positioned in sealed engagement with the delivery device and the delivery port is positioned in fluid communication with a fluid passageway of the delivery device.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIGS. 22A-22B are an illustration of one embodiment of a pin;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION OF THE EXEMPLARY EMBODIMENTS

The terms "drug", "medication", "fluid", "liquid" and/or "therapeutic fluid" are used synonymously to refer to any substance contained within the reservoir or container. The term "drug reservoir", "reservoir" and "container" are also used synonymously to refer to element 110.

Various embodiments are described and shown herein for a container and/or reservoir for holding fluid and a device/system/method for connecting the container and/or reservoir to a device for delivering and/or pumping the fluid from the container and/or reservoir to, for example, a patient/user. Various devices may be connected to the container and/or reservoir, including but not limited to, those shown and described in U.S. Pat. No. 8,414,522, issued Apr. 9, 2013 and entitled Fluid Delivery Systems and Methods; U.S. Pat. No. 8,491,570, issued Jul. 23, 2013 and entitled Infusion Pump Assembly; and U.S. patent application Ser. No. 13/788,260, filed Mar. 7, 2013 and entitled Infusion Pump Assembly, now U.S. Publication No. US-2014-0107579, published Apr. 17, 2014; each of which is hereby incorporated herein by reference in its entirety.

Figure 1:
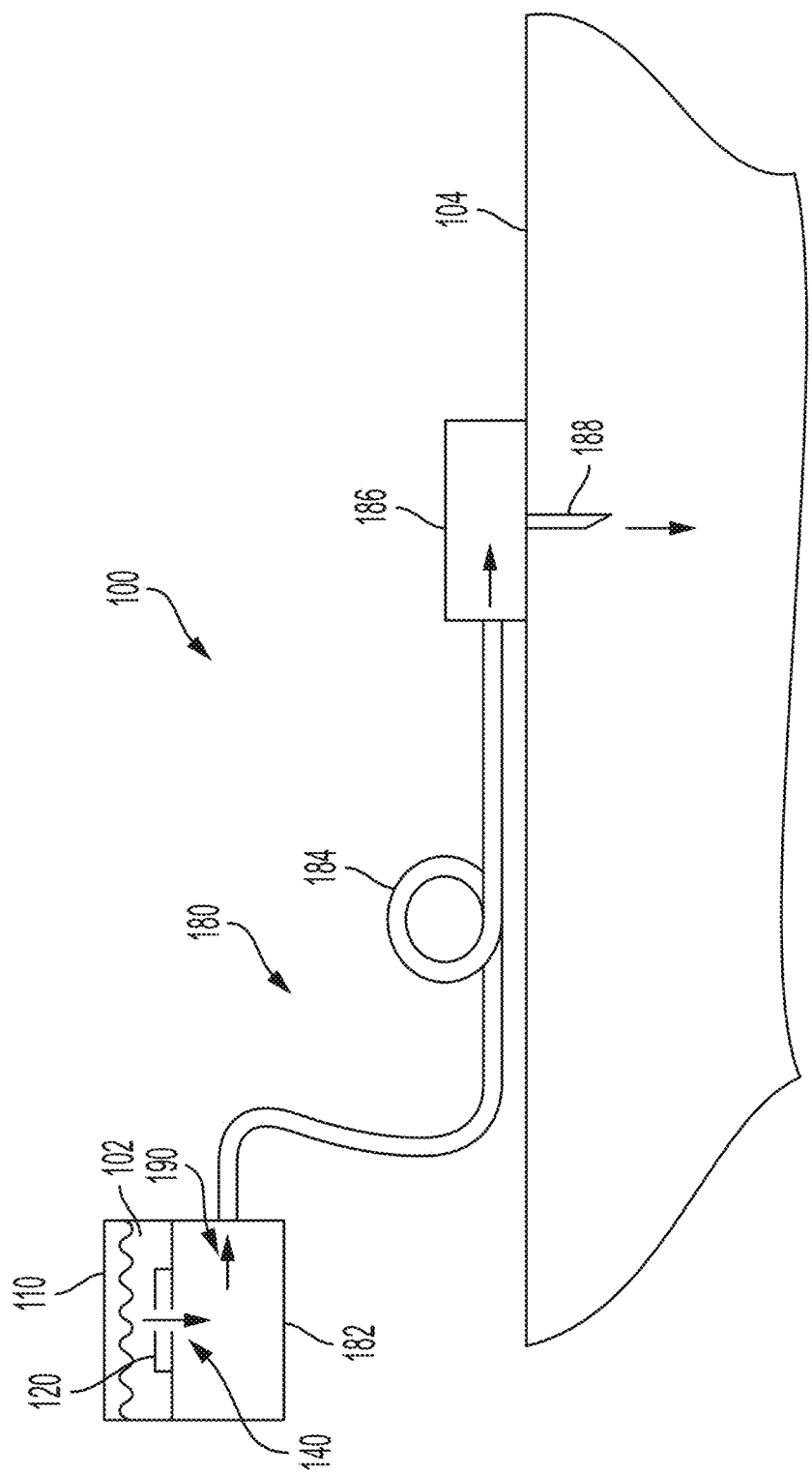
FIG. 1 is a schematic view of a drug delivery system for delivering medication to a patient, the delivery system including a container configured to hold the medication, an intermediate port connector, and a delivery device with a drive mechanism.

Referring to FIG. 1, a parenteral drug delivery system 100 is shown for delivering medication 102, which may include, but is not limited to, basal and/or bolus insulin formulations or other liquid/fluid medications, into a user's skin 104.

Delivery system 100 includes a container assembly having a drug reservoir or container 110 coupled to an intermediate port connector 120. Delivery system 100 further includes a delivery device 180 with a drive mechanism 182 configured to move medication 102 from container 110 to the user 104. Further detail of the elements of delivery system 100 are described below.

Container 110 of delivery system 100 is configured to hold medication/fluid 102. Container 110 may be constructed of one or more flexible materials, such as cyclo olefin polymers (COP), cyclic olefin copolymers (COC), or other pharmaceutically suitable materials. Container 110 may also be coated (e.g., laminated or coextruded) with a pharmaceutically suitable film, such as a poly-chloro-tri-fluoro-ethylene (PCTFE) film (e.g., Aclar). The PCTFE layer may serve as a water barrier to provide moisture vapor retention. In illustrated embodiment, container 110 is substantially flat in an unfilled state and expands when in a filled state. In one embodiment, the flexibility of container 110 is achieved with an elastomeric tie layer in addition to the COP or COC material layer. In another embodiment, the container flexibility is provided with a softer material layer, such as low density polyethylene (LDPE) multilayered with the COP or COC. In some embodiments, the multilayer construction of container 110 includes an outer PCTFE layer (e.g., 20 micrometers (μm) thick), an inner COP layer (e.g., 15 μm) adapted to contact the contained drug, an intermediate adhesive layer adjacent the PCTFE, layer, and an intermediate linear LDPE layer (e.g., 25 μm) between the adhesive layer and the COP. In some embodiments, the multilayer construction of container 110 includes an elastomeric tie-layer positioned in place of or adjacent to the adhesive layer. In some embodiments, the multilayer construction of container 110 includes an outer PCTFE layer, an inner COC layer (e.g., 20 μm) adapted to contact the contained drug, and an elastomeric tie-layer between the PCTFE and COC layers. Any other configurations may be used in various embodiments.

In some embodiments, container 110 may have a generally flat shape resembling a bag, but in various embodiments, the shape may vary. According to one embodiment, container 110 is pre-filled with fluid/medication 102 before being supplied to a user 104. However, in some embodiments, container 110 may be filled manually by caregiver/user 104. One embodiment of a filling process is described below.

In some embodiments, port connector 120 of the container assembly may be constructed of one or more rigid thermoplastic materials, such as COP or COC material which contacts the drug in container 110. In some embodiments, port connector 120 may also include portions made of flexible elastomeric materials. In various embodiments, port connector 120 may be fixedly coupled (e.g., heat sealed, adhered, ultrasonic welded, or any other method of fixedly coupling) to container 110 and removably coupled to delivery device 180. In some embodiments, port connector 120 is comprised of COP or COC material which contacts the corresponding COP or COC layer of container 110 when coupled together. In various embodiments, port connector 120 includes a first filling port (for example, in some embodiments, port connector 120 includes a septum) configured to convey medication 102 from a filling apparatus (not shown) into container 110 during the drug filling process. In various embodiments, port connector 120 also includes a second delivery port configured to convey medication 102 from container 110 to delivery device 180 when the components are coupled together following the connection process. Both the filling process and the connection process are described further below.

In some embodiments, delivery device 180 of the illustrative delivery system 100 is an infusion-type pump device. In various embodiments, delivery device 180 may be any one or more of the infusion devices and systems shown and described in any one or more of Appendices A-C. Drive mechanism 182 of such an infusion-type delivery device 180 may include a motor-operated and/or valve controlled pump, for example. As shown in FIG. 1, the infusion-type delivery device 180 may also include a flexible tube 184, an infusion base 186 that rests upon or adheres to the user's skin 104, and an infusion needle/catheter 188, that extends into the patient's skin 104. In various embodiments, delivery device 180 is an injection-type device, such as a bolus injector. Drive mechanism 182 of such an injection-type delivery device 180 may include a button-operated piston, a spring, a chemical engine, and/or other suitable drive mechanisms, for example.

Referring now also to FIGS. 2-6, one embodiments of a port connector 120 is shown. In various embodiments, the port connector 120 may include a fill port 130 in fluid communication with a container 110 (shown in phantom). The fill port 130 may be used to the fill container 110 with medication 102 during the filling process, which is described below. In some embodiments, the port connector 120 may also include a delivery or outlet port 140 having an inlet 142 in fluid communication with container 110 and an outlet 144 in selective fluid communication with delivery device 180. The delivery port 140 may be used to convey medication 102 from container 110 to delivery device 180 during a delivery process.

Figure 2:
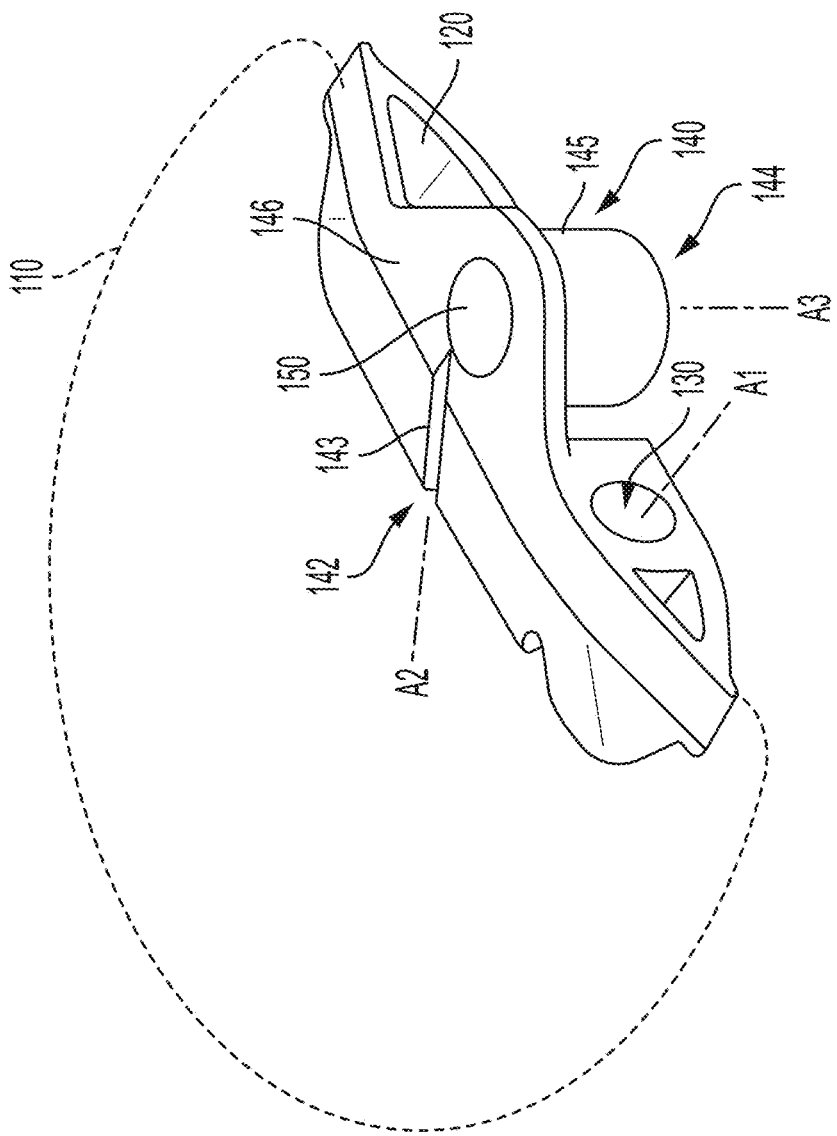
FIG. 2 is a perspective view of a first exemplary port connector coupled to a container.
Figure 3:
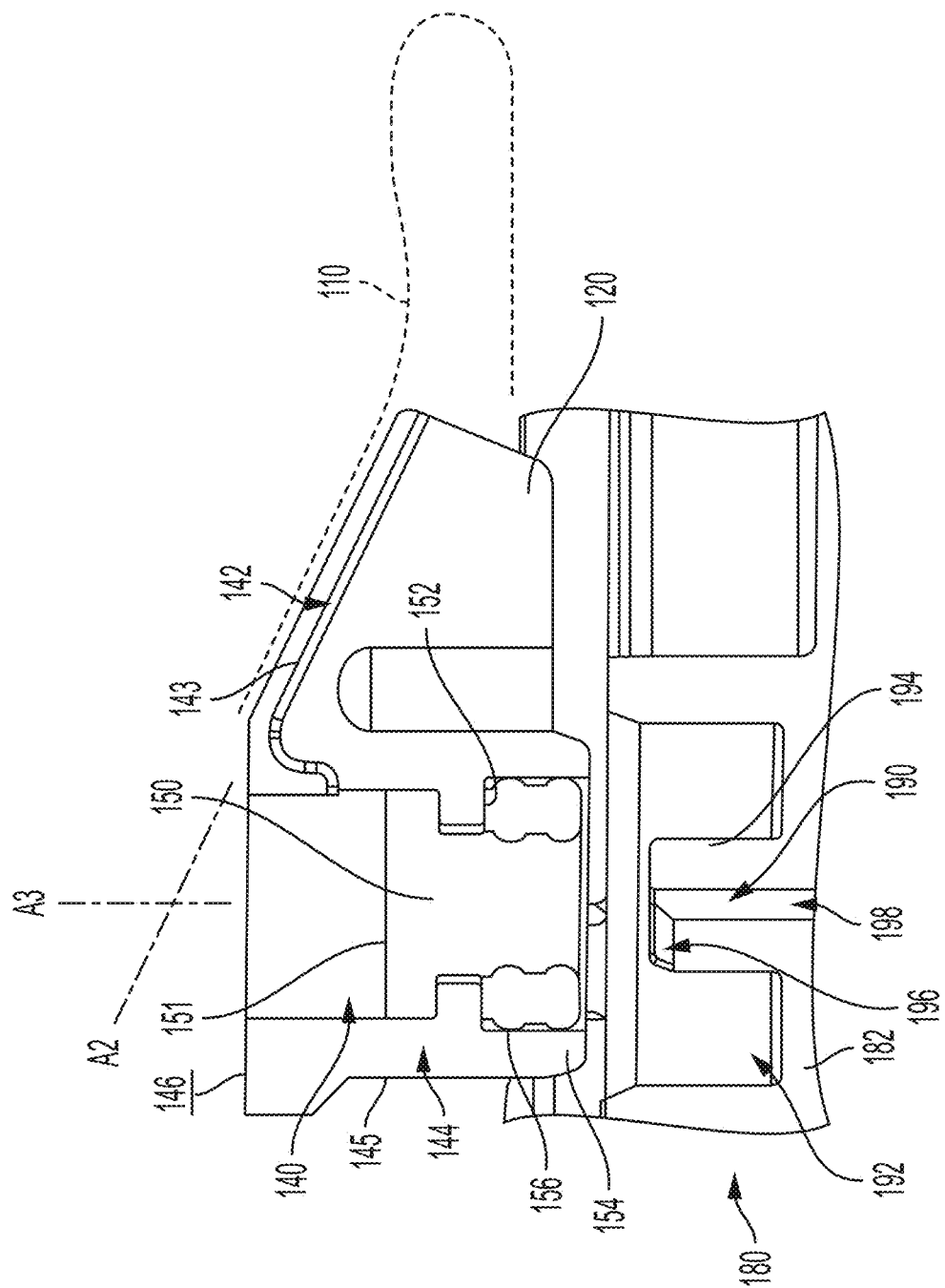
FIG. 3 is a sectional view of the first port connector of FIG. 2 in a sealed configuration and spaced apart from a port of a corresponding delivery device.

Referring now also to FIGS. 2 and 3, in various embodiments, fill port 130 is arranged along a first axis A1, inlet 142 of delivery port 140 is arranged along a second axis A2, and outlet 144 of delivery port 140 is arranged along a third axis A3. In various embodiments, where the first axis A1 is oriented at 0 degrees, the second axis A2 may be oriented at about 45 degrees and the third axis A3 may be oriented perpendicular to first axis A1 at about 90 degrees. However, in various embodiments, the orientation of fill port 130 and delivery port 140 may vary.

In various embodiments, inlet 142 of delivery port 140 may be at least partially defined by wall 143 of port connector 120. A partial wall 143 is shown in FIG. 2, with the rest of inlet 142 being defined by container 110 (shown in phantom). In some embodiments, inlet 142 is defined entirely by wall 143 of port connector 120.

In various embodiments, outlet 144 of delivery port 140 may be defined by wall 145 of port connector 120. Wall 145 is cylindrical, as shown in the embodiments shown in FIGS. 2-3, however, in other embodiments; wall 145 may be any shape. As shown in FIG. 3, outlet 144 of delivery port 140 illustratively includes a pin 150 with a head 151 configured to move along axis A3, a shoulder 152 that extends radially inward from wall 145, a first seal 154 (e.g., a first O-ring) positioned around pin 150 and below shoulder 152, and a second seal 156 (e.g., a second O-ring) also positioned around pin 150 and below shoulder 152. In various embodiments, first seal 154 and second seal 156 may be separate components, however, in some embodiments, first seal 154 and second seal 156 may be coupled together as a single integral component. In one embodiment, seals 154, 156 are made of flexible elastomeric material. However, in various embodiments, seals 154, 156 may be made from any material.

Referring now also to FIGS. 3-6, an exemplary connection and delivery process performed using port connector 120 is described below.

FIG. 3 shows port connector 120 in a sealed configuration, wherein outlet 144 of delivery port 140 is sealed closed, and disconnected from the delivery device 180. In various embodiments, the first seal 154 and second seal 156 are both positioned in sealed engagement with wall 145 and pin 150 of delivery port 140 (i.e., illustratively positioned between wall 145 and pin 150) to close outlet 144 of delivery port 140. However, in other embodiments, the first seal 154 and second seal 156 may be positioned differently. Using first seal 154 and second seal 156 in combination around pin 150 forms primary and back-up seals that maintain the integrity of delivery port 140 even in the event of a seal failure. In this sealed configuration, first seal 154 and second seal 156 may block medication 102 (FIG. 1) in container 110 from escaping through the closed outlet 144 of delivery port 140. Also, first seal 154 and second seal 156 may block contaminants from entering container 110 through the closed outlet 144 of delivery port 140 to maintain the integrity of medication 102 (FIG. 1). In various embodiments, container 110 and port connector 120 may be stored in this sealed configuration for several weeks, months, or years, for example.

Figure 4:
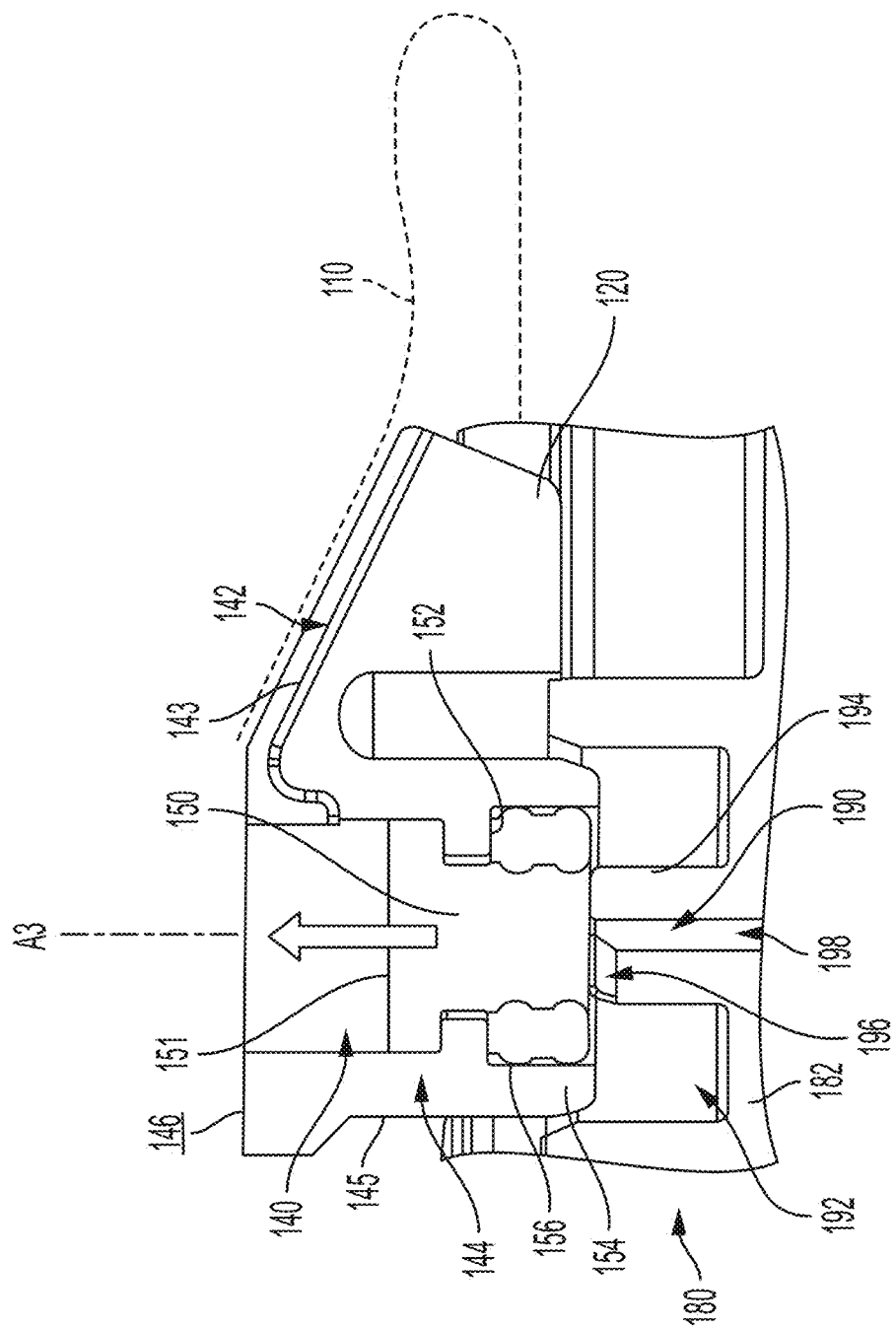
FIG. 4 is a sectional view of the first port connector of FIG. 2 in an aligned and sealed configuration wherein the port of the first port connector is aligned with the port of the corresponding delivery device.

FIG. 4 shows port connector 120 in an aligned and sealed configuration, wherein outlet 144 of delivery port 140 is aligned with fluid passageway 190 of delivery device 180. The illustrative delivery device 180 includes a socket 192 that is sized and shaped to receive wall 145 of port connector 120 in the aligned configuration and subsequent configurations. The illustrative delivery device 180 also includes a post 194 that is centrally located in socket 192 and configured to engage pin 150 along axis A3. In the embodiment shown in FIG. 4, fluid passageway 190 follows an L-shaped path through post 194, with a first portion 196 of fluid passageway 190 traveling radially inward through post 194 in a direction perpendicular to axis A3 and a second portion 198 of fluid passageway 190 traveling axially through post 194 along axis A3. The delivery port 140, socket 192, and post 194 are configured to cooperate to form the port connection between container 110 and the delivery device 180, as disclosed in greater detail herein.

Figure 5:
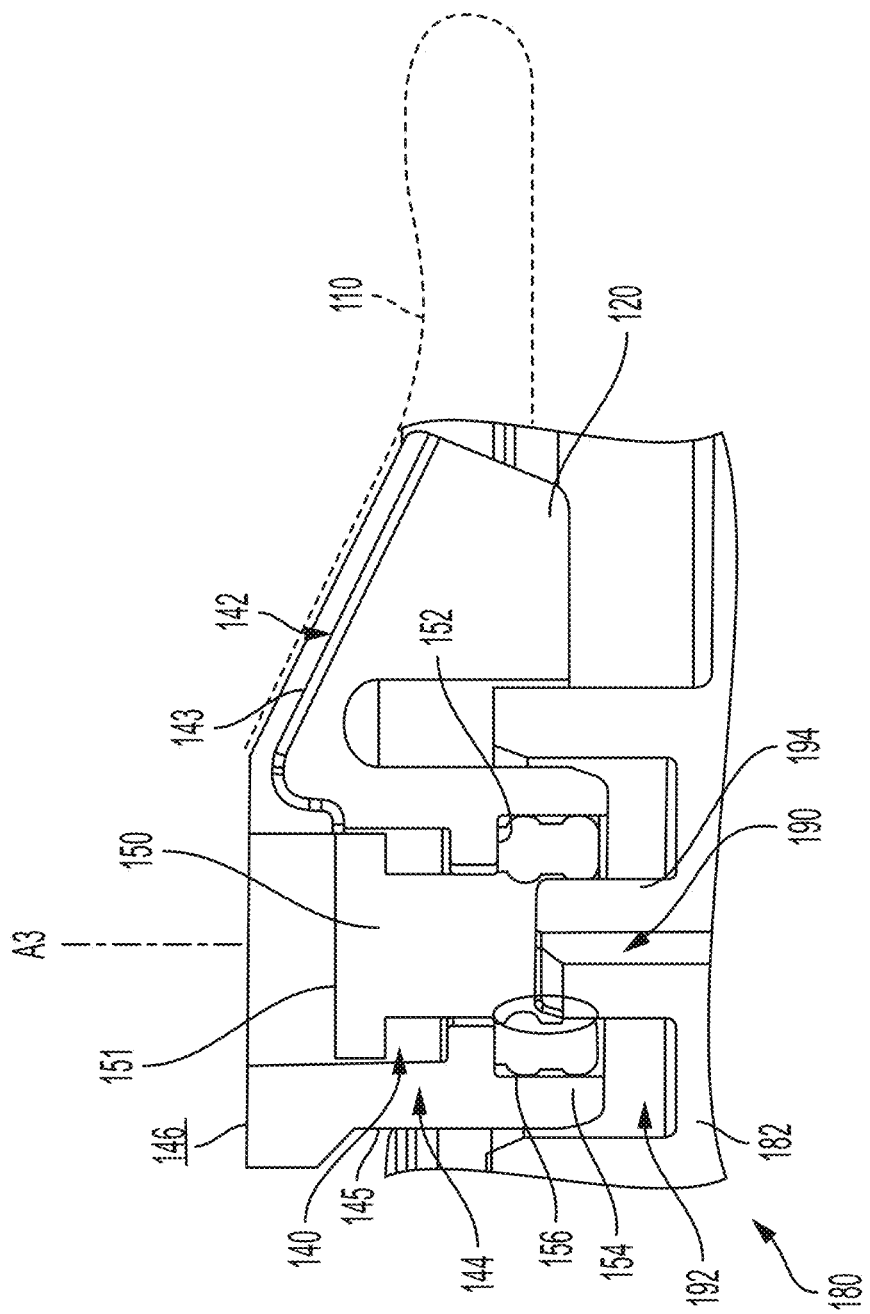
FIG. 5 is a sectional view of the first port connector of FIG. 2 in an intermediate configuration with the corresponding delivery device.

Referring now also to FIG. 5, the port connector 120 is in an intermediate configuration, wherein delivery port 140 of port connector 120 forms a sealed connection with delivery device 180. In the embodiment shown in FIG. 5, this intermediate configuration is achieved by a downward force on upper surface 146 of port connector 120 along axis A3 and moving wall 145 of port connector 120 into socket 192 of delivery device 180. This downward movement is transferred to shoulder 152, first seal 154, and second seal 156 of port connector 120. However, pin 150 of port connector 120 contacts post 194 of delivery device 180 and is prevented from traveling downward into delivery device 180. As a result, first seal 154 and second seal 156 move downward relative to pin 150 of port connector 120 and toward post 194 of delivery device 180. In the intermediate configuration shown in FIG. 5, first seal 154 separates from pin 150 of port connector 120 and moves into sealed engagement with post 194 of delivery device 180, while second seal 156 remains in sealed engagement with pin 150 of port connector 120. Thus, port connector 120 forms a convenient, reliable, sealed connection with delivery device 180 while also maintaining the sealed delivery port 140 to block fluid flow through port 140.

Figure 6:
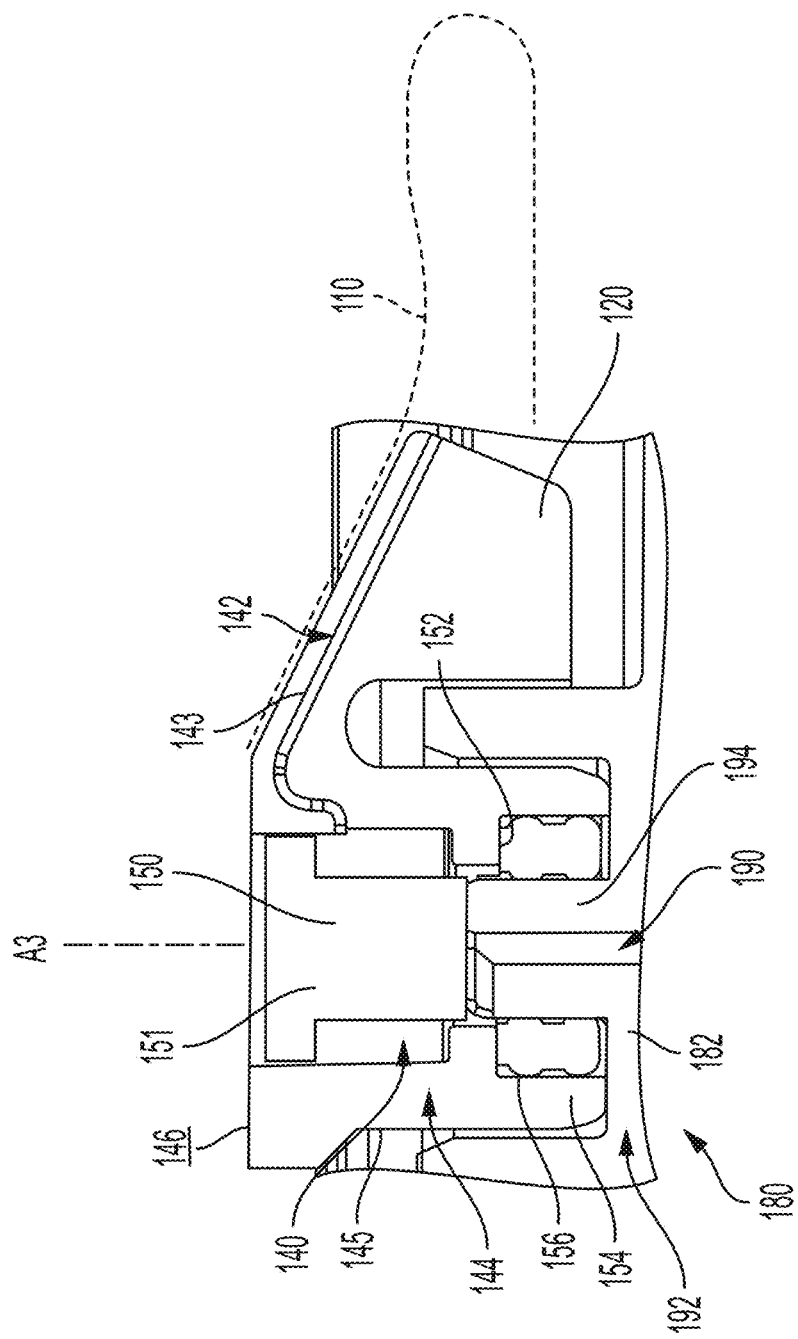
FIG. 6 is a sectional view of the first port connector of FIG. 2 in a delivery configuration with the corresponding delivery device.

Referring now also to FIG. 6, port connector 120 is in a final or delivery configuration, wherein delivery port 140 of port connector 120 forms a fluid connection with fluid passageway 190 of delivery device 180. In this embodiment, the delivery configuration is achieved by the continued downward force on upper surface 146 of port connector 120 along axis A3 until wall 145 of port connector 120 is seated in socket 192 of delivery device 180. As in the above-described intermediate configuration, this downward movement is transferred to shoulder 152, first seal 154, and second seal 156 of port connector 120. In the delivery configuration of FIG. 6, first seal 154 and second seal 156 both separate from pin 150 of port connector 120 (i.e., move axially apart from pin 150) and move into sealed engagement with post 194 of delivery device 180. Inlet 142 of delivery port 140 is now exposed to fluid passageway 190 of delivery device 180 through the open outlet 144 of delivery port 140. Stated differently, inlet 142 of delivery port 140 is now placed in fluid communication with fluid passageway 190 of delivery device 180. In use, medication 102 (FIG. 1) from container 110 is free to travel through delivery port 140 around the freed pin 150 of port connector 120 and into fluid passageway 190 of delivery device 180. Using first seal 154 and second seal 156 in combination around post 194 forms primary and back-up seals that maintain the integrity of fluid passageway 190 even in the event of a seal failure.

Port connector 120 may present certain benefits/advantages in addition to those discussed above. For example, port connector 120 may have a small size and a small dead-volume, which may enable use in tight spaces. Also, port connector 120 may be constructed with rigid, well-toleranced thermoplastic parts, which may enable robust operation with minimal debris. In the illustrative embodiment, the force to create the port connection is applied through the rigid parts, for example, rigid post 182 pushes on rigid pin 150, rather than through flexible or elastomeric parts. Further, only a small portion of the elastomeric seal (154, 156) comes into contact with the fluid throughout the positioning of container 110 from the sealed configuration to the delivery configuration; accordingly, the fluid exerts minimal, if any, shear on the elastomeric seals.

Figure 7:
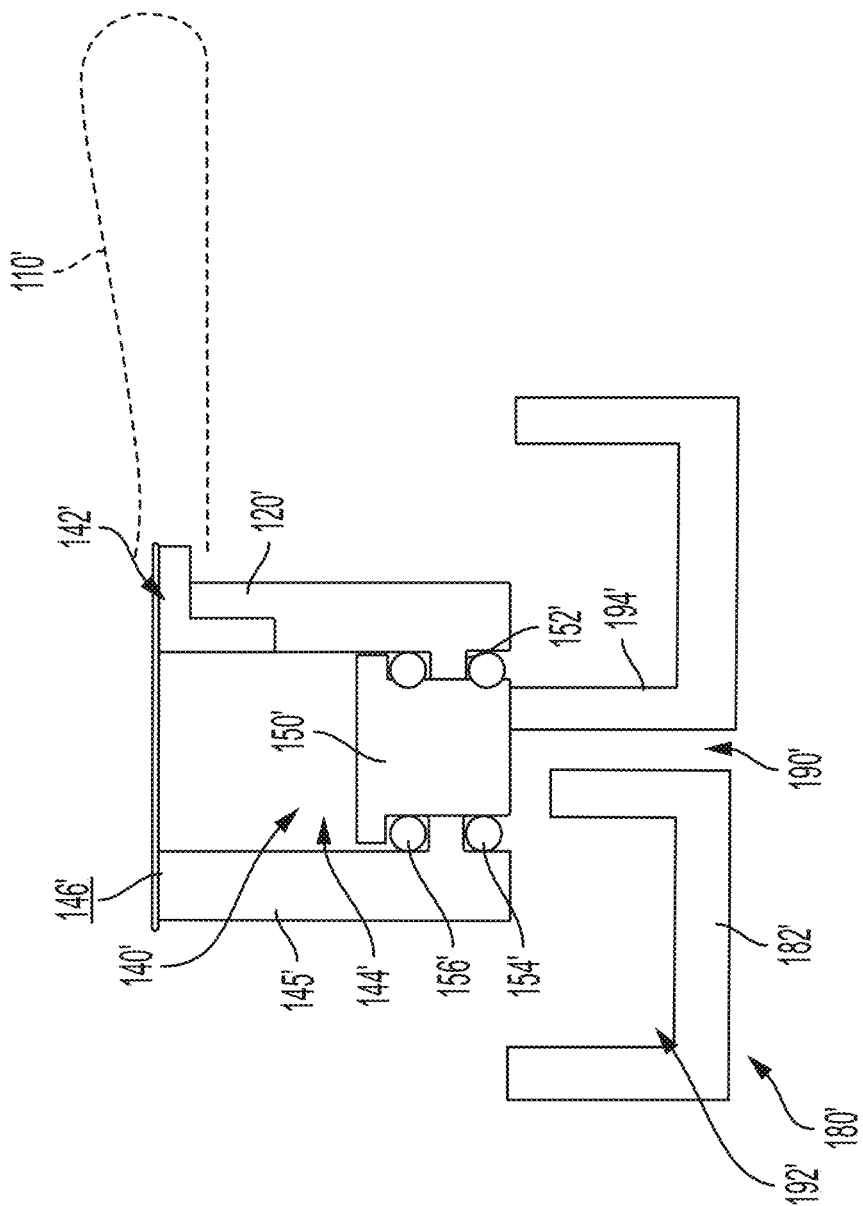
FIG. 7 is a sectional view of a second exemplary port connector in an aligned and sealed configuration wherein a port of the second port connector is aligned with a port of a corresponding delivery device.
Figure 8:
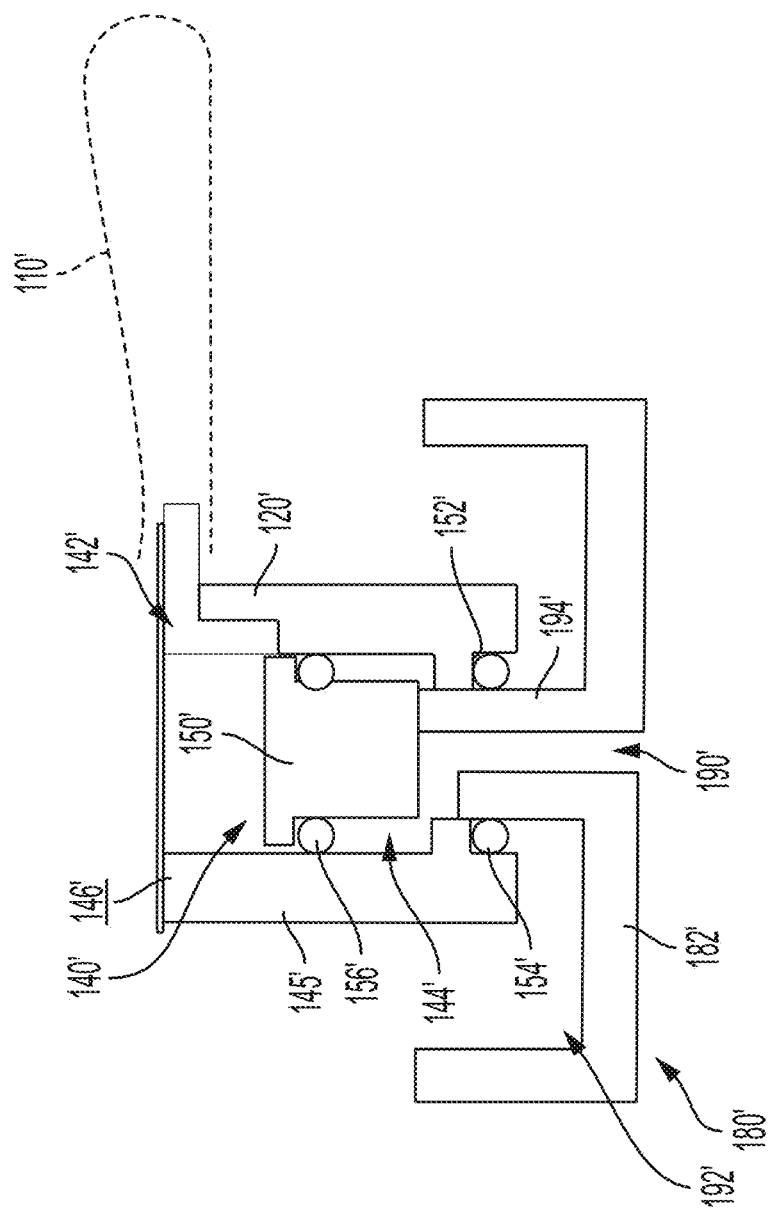
FIG. 8 is a sectional view of the second port connector of FIG. 7 in an intermediate configuration with the corresponding delivery device.
Figure 9:
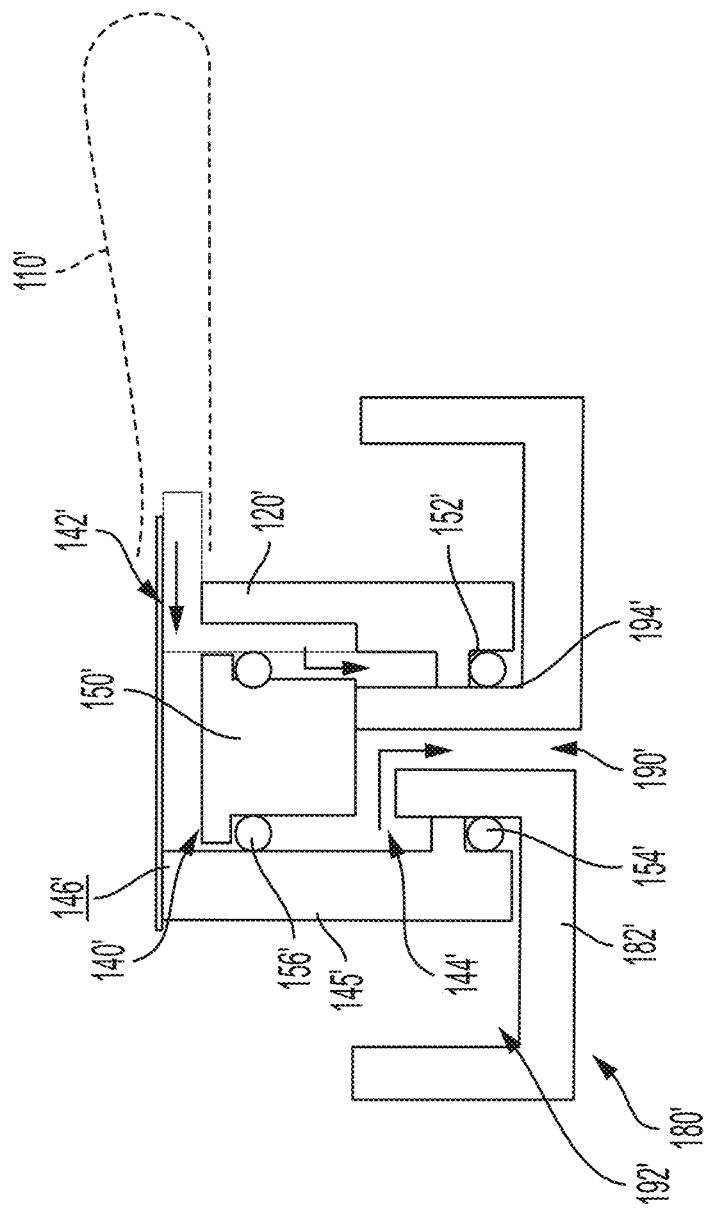
FIG. 9 is a sectional view of the second port connector of FIG. 7 in a delivery configuration with the corresponding delivery device.
Figure 10:
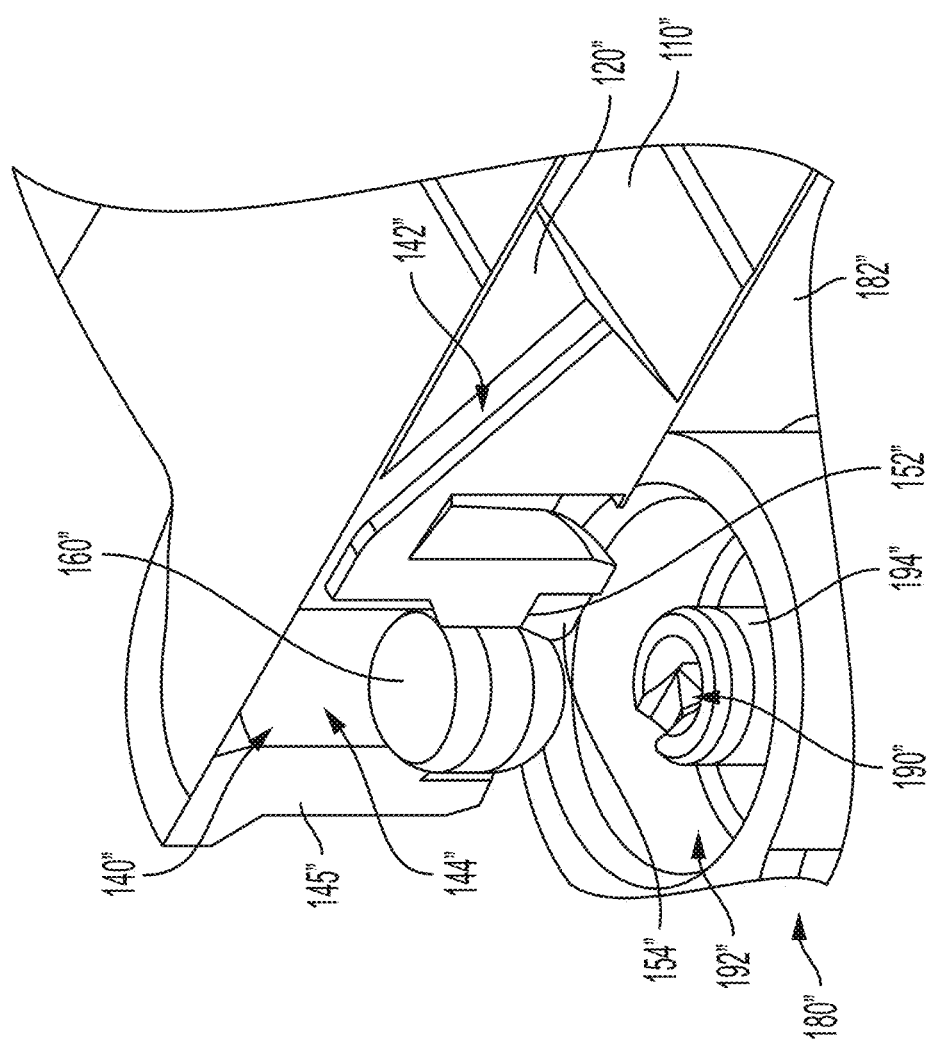
FIG. 10 is a sectional perspective view of a third exemplary port connector coupled to a container and spaced apart from a corresponding delivery device.
Figure 11:
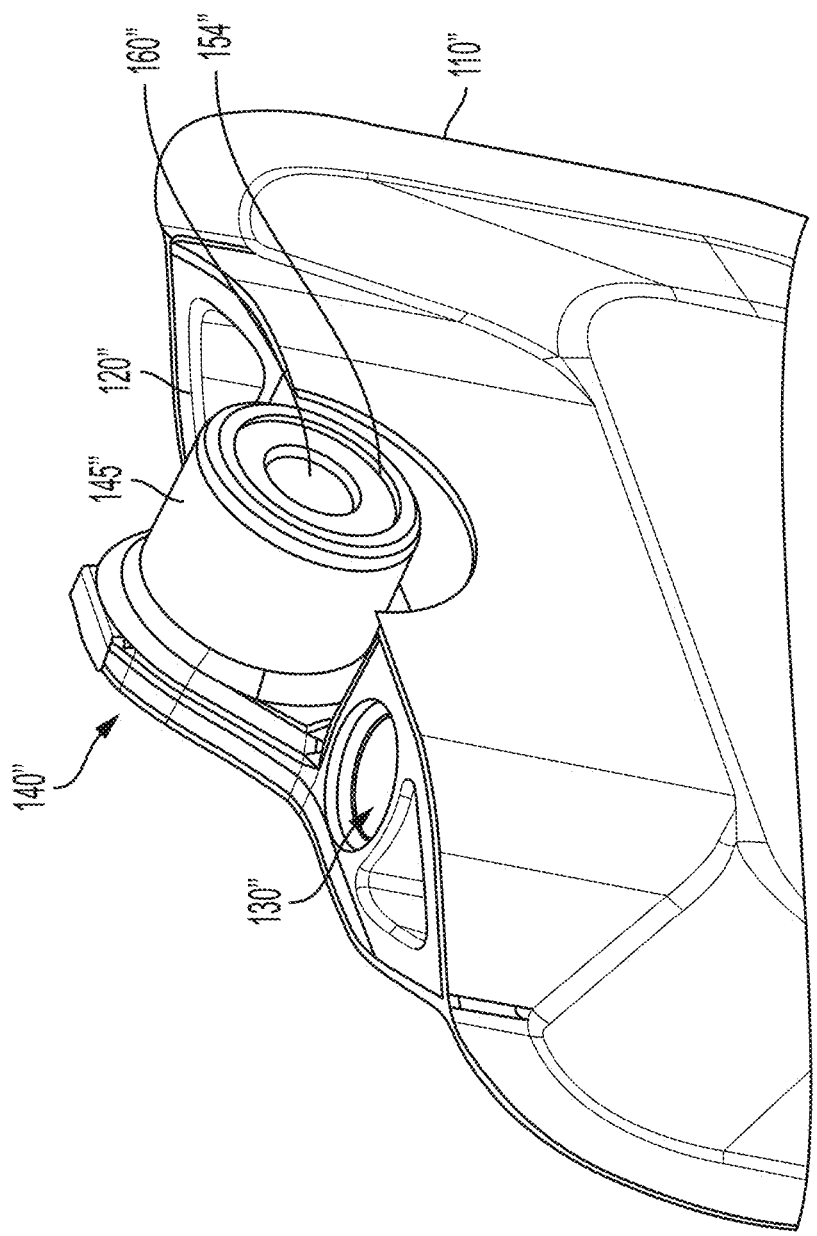
FIG. 11 is a bottom perspective view of the third port connector and the container of FIG. 10.
Figure 12:
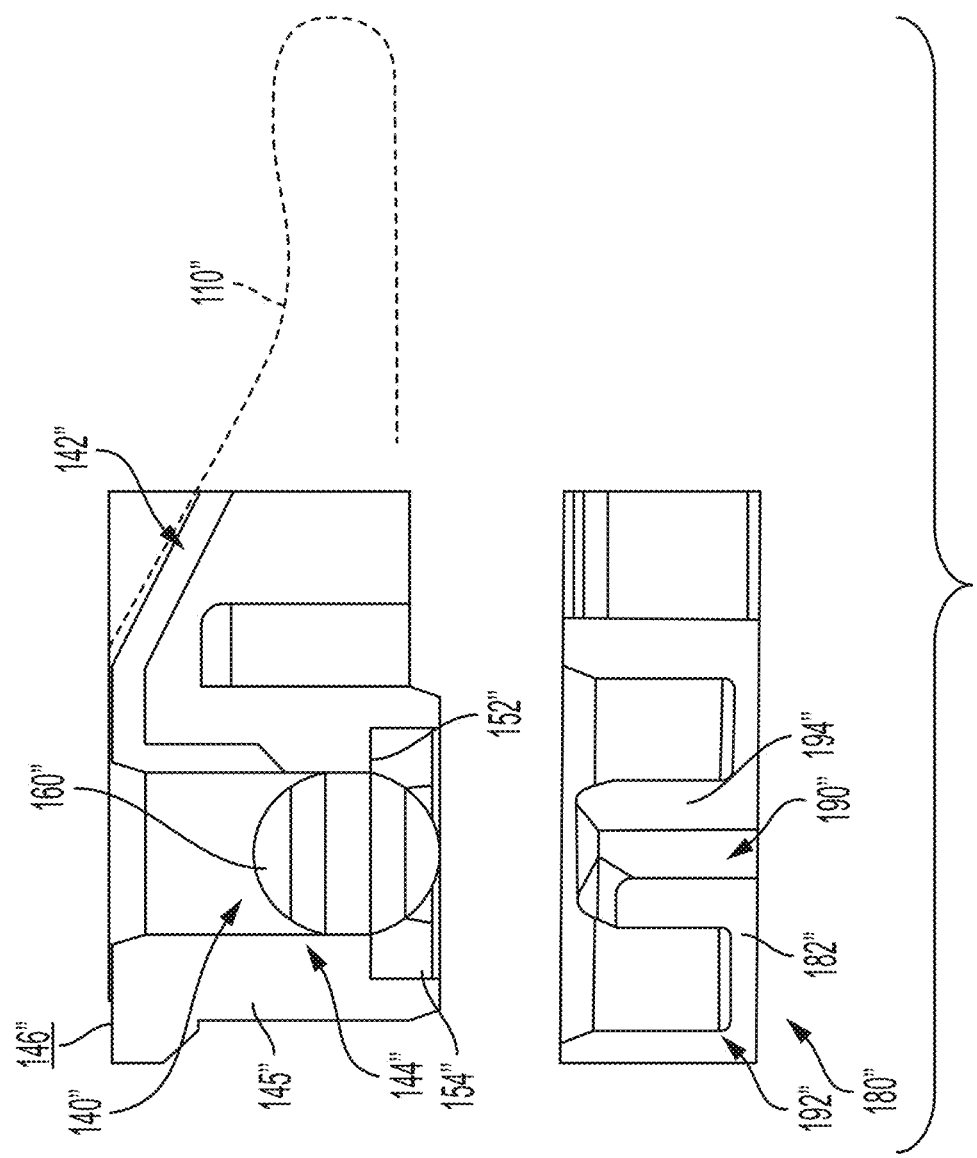
FIG. 12 is a sectional view of the third port connector of FIG. 10 in a sealed configuration and spaced apart from a port of the corresponding delivery device.
Figure 13:
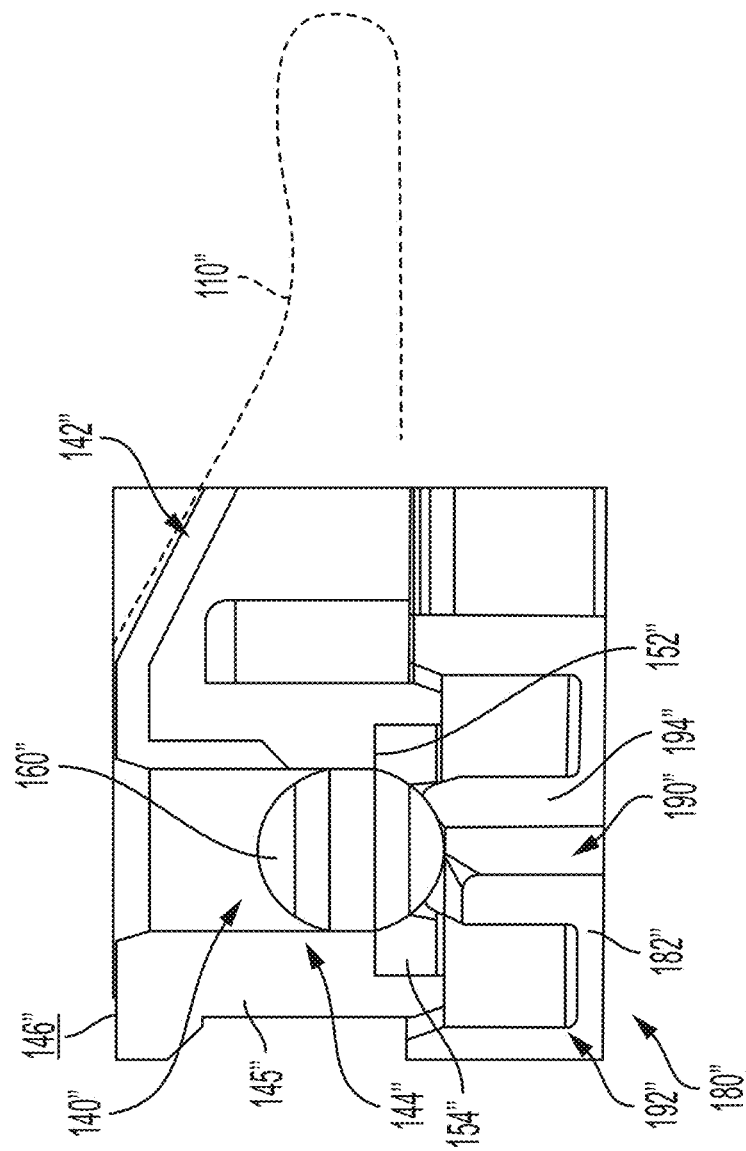
FIG. 13 is a sectional view of the third port connector of FIG. 10 in an aligned and sealed configuration wherein a port of the third port connector is aligned with the port of the corresponding delivery device.
Figure 14:
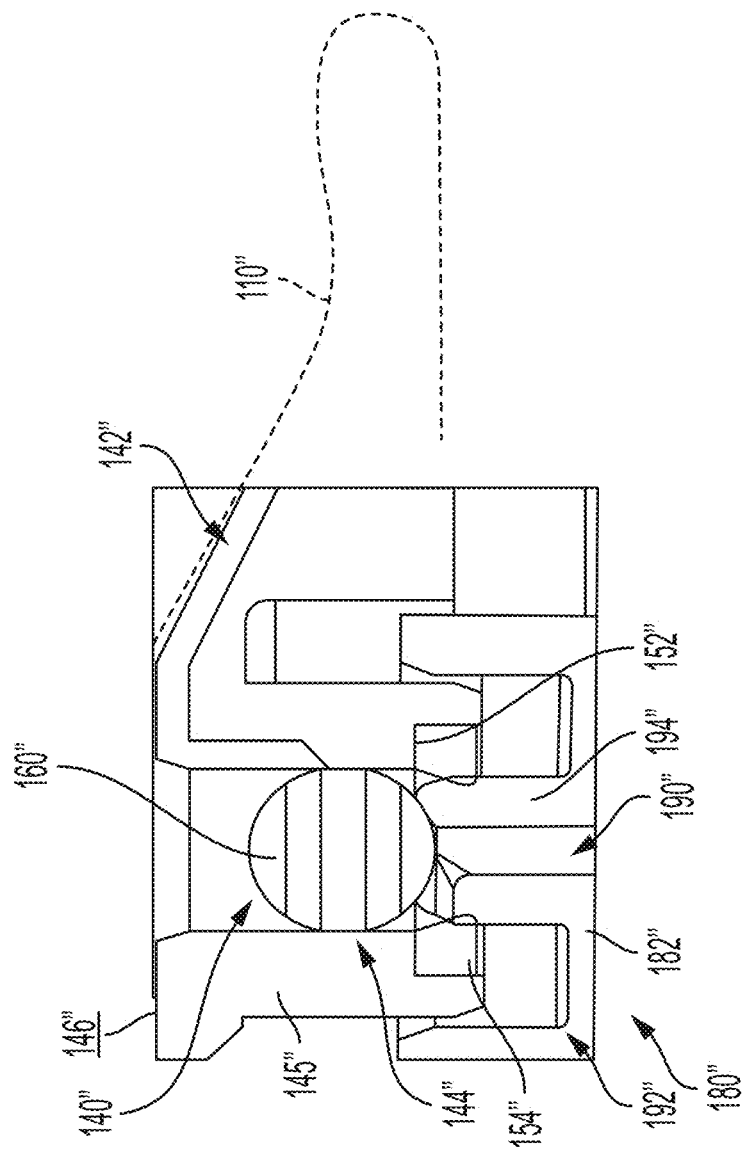
FIG. 14 is a sectional view of the third port connector of FIG. 10 in an intermediate configuration with the corresponding delivery device.
Figure 15:
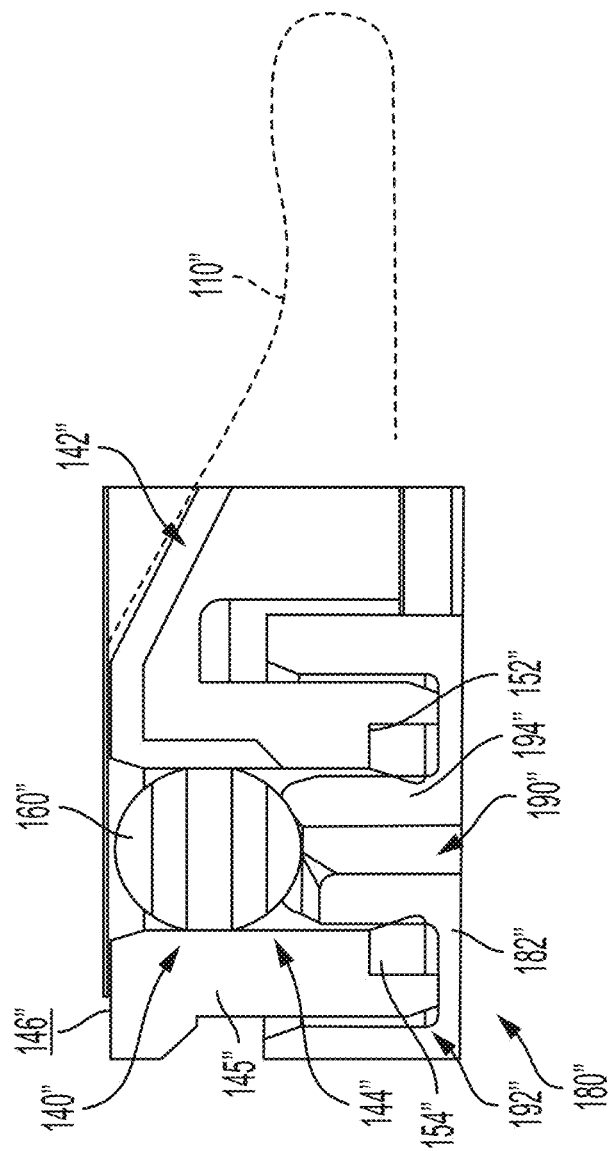
FIG. 15 is a sectional view of the third port connector of FIG. 10 in a delivery configuration with the corresponding delivery device.

Another exemplary port connector 120' is shown in FIGS. 7-9. The second port connector 120' is similar to the above-described first port connector 120, with like reference numerals identifying like elements, except as described below. Port connector 120' includes a delivery port 140' having an inlet 142' and an outlet 144'. Delivery port 140' of port connector 120' includes a moveable pin 150', a shoulder 152', a first seal 154', and a second seal 156'. In FIG. 3, seals 154 and 156 of the first port connector 120 were positioned together below shoulder 152. In FIG. 7, by contrast, seals 154' and 156' of the second port connector 120' are separated and positioned on opposing sides of shoulder 152'. More specifically, first seal 154' is positioned below shoulder 152', and second seal 156' is positioned above shoulder 152'.

The connection process associated with the second port connector 120' is similar to the connection process associated with the above-described first port connector 120, except as described below. In the aligned and sealed configuration of FIG. 7, first seal 154' and second seal 156' are both positioned in sealed engagement with pin 150' and wall 145' of port connector 120'. In the intermediate configuration of FIG. 8, first seal 154' moves into sealed engagement with post 194' of delivery device 180' and remains sealingly engaged with wall 145', while second seal 156' remains in sealed engagement with pin 150' and wall 145' of port connector 120'. In the delivery configuration of FIG. 6, first seal 154 and second seal 156 of the first port connector 120 both moved into sealed engagement with post 194 of delivery device 180. In the delivery configuration of FIG. 9, by contrast, second seal 156' remains in sealed engagement with pin 150' and wall 145' of the second port connector 120'. However, inlet 142' of port connector 120' opens downward below second seal 156', which exposes inlet 142' of port connector 120' to fluid passageway 190' of delivery device 180'. In use, medication 102 (FIG. 1) from container 110' is free to travel through delivery port 140' below second seal 156' of port connector 120' and into fluid passageway 190' of delivery device 180'.

A third exemplary port connector 120" is shown in FIGS. 10-15. The third port connector 120" is similar to the above-described port connectors 120 and 120', with like reference numerals identifying like elements, except as described below. Port connector 120" includes a delivery port 140" having an inlet 142" and an outlet 144". Delivery port 140" of port connector 120" includes a wall 145", a shoulder 152", and a first seal 154". Additionally, delivery port 140" of port connector 120" includes a moveable ball seal 160".

The connection process associated with the third port connector 120" is similar to the connection processes associated with the above-described port connectors 120 and 120', except as described below. In the sealed configuration of FIG. 12 and the aligned configuration of FIG. 13, first seal 154" and ball seal 160" are both positioned in sealed engagement with wall 145" of port connector 120". In the intermediate configuration of FIG. 14, first seal 154" moves into sealed engagement with post 194" of delivery device 180", while ball seal 160" remains in sealed engagement with wall 145" of port connector 120". In the delivery configuration of FIG. 15, inlet 142" of port connector 120" moves downward below ball seal 160", which exposes inlet 142" of port connector 120" to fluid passageway 190" of delivery device 180". In use, medication 102 (FIG. 1) from container 110" is free to travel through delivery port 140" below ball seal 160" of port connector 120" and into fluid passageway 190" of delivery device 180".

Figure 16:
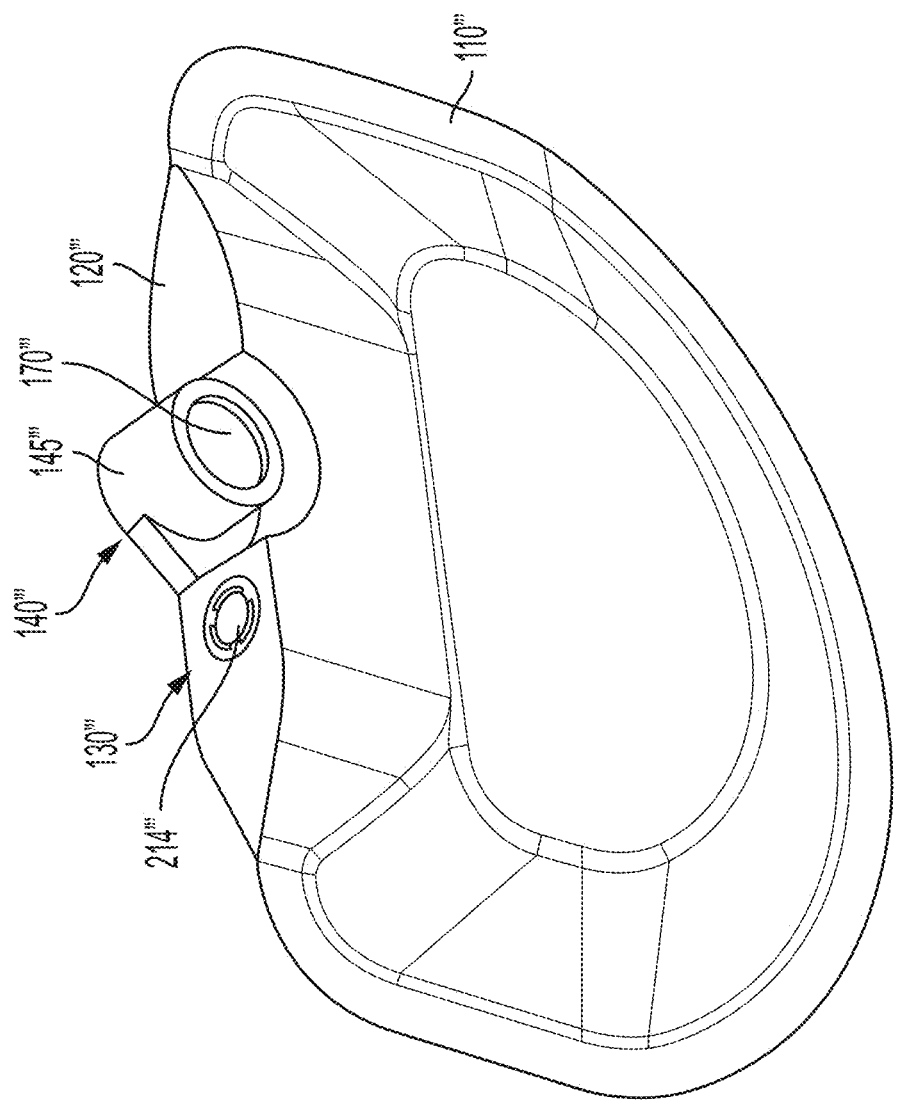
FIG. 16 is a bottom perspective view of a fourth exemplary port connector coupled to a container.
Figure 17:
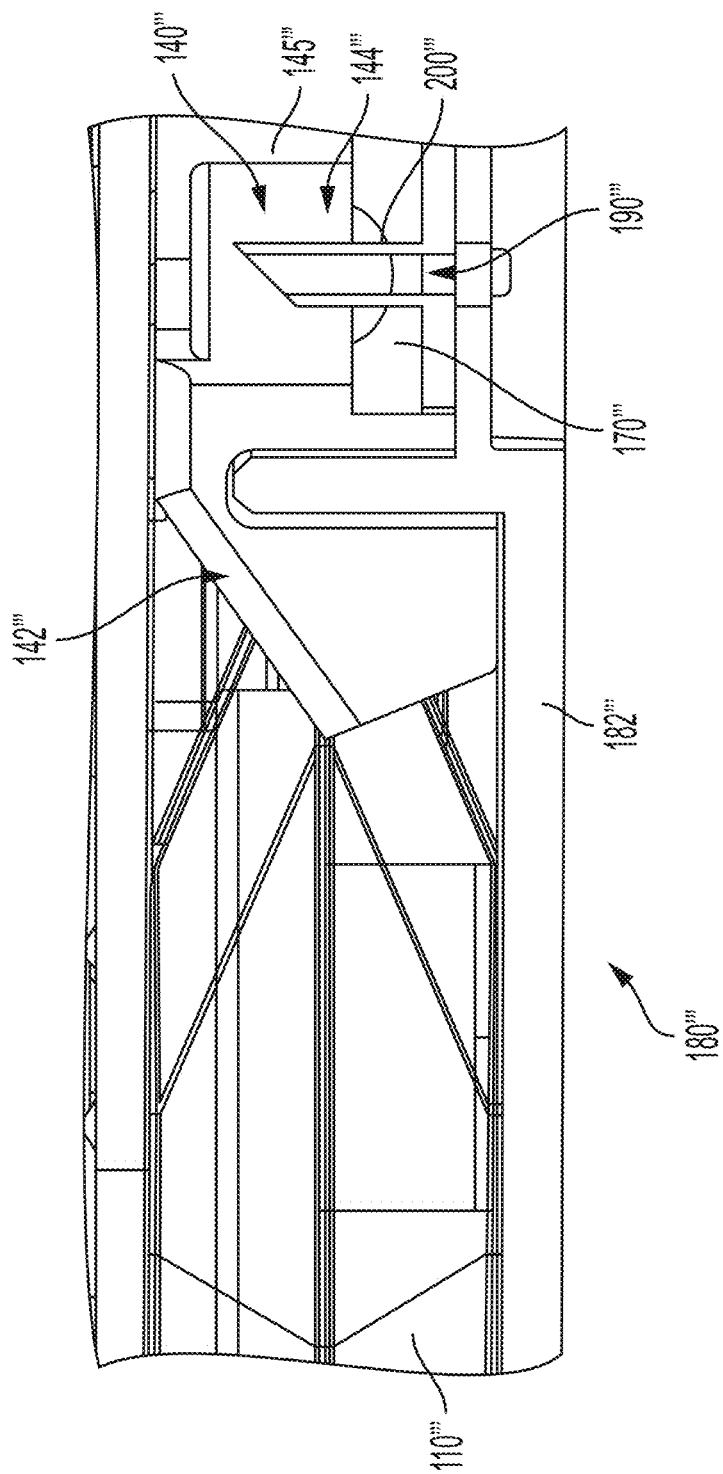
FIG. 17 is a sectional view of the fourth port connector of FIG. 16 in a delivery configuration with a corresponding delivery device.

A fourth exemplary port connector 120''' is shown in FIGS. 16-17. The fourth port connector 120''' is similar to the above-described port connectors 120, 120''', and 120''', with like reference numerals identifying like elements, except as described below. Port connector 120''' includes a delivery port 140''' having an inlet 142''' and an outlet 144'''. Delivery port 140''' of port connector 120''' includes a plug or septum 170''' (e.g., butyl elastomer material) configured to selectively interact with needle 200''' of delivery device 180'''. Port connector 120''' may have a sealed configuration (not shown), in which septum 170''' seals outlet 144''' of delivery port 140'''. Port connector 120''' may also have a delivery configuration, as shown in FIG. 17, in which needle 200''' punctures septum 170''' to expose outlet 144''' of delivery port 140''' to fluid passageway 190''' in needle 200''' of delivery device 180'''.

An exemplary filling process performed using a port connector to fill a container with medication will now be described with reference to FIGS. 18-21. While reference is made to port connector 120 in FIGS. 18-21, it is understood that the filling process may be performed using any of the other above-described port connectors 120', 120", and 120'''.

Figure 19:
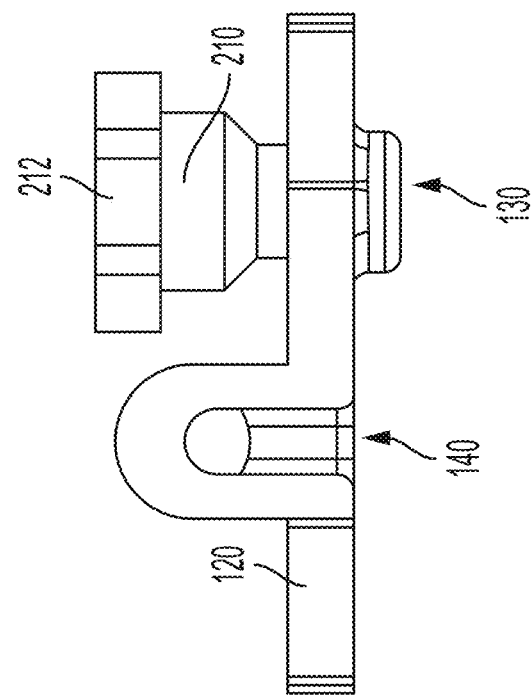
FIG. 19 is a top plan view of the port connector and the filling adapter of FIG. 18.
Figure 18:
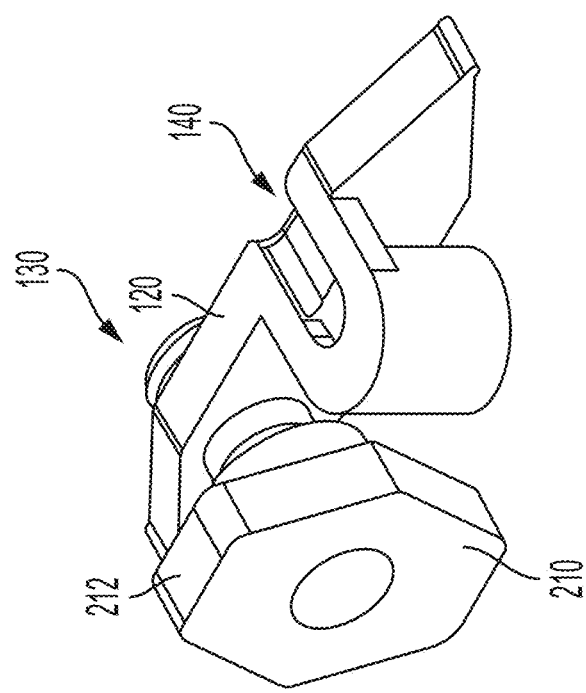
FIG. 18 is a perspective view of a port connector coupled to a filling adapter in a filling configuration.

Referring now also to FIGS. 18 and 19 show port connector 120 in an open or filling configuration, wherein a filling adapter 210 is positioned in fluid communication with an open fill port 130 of port connector 120. Outer surface 212 of adapter 210 is configured to frictionally engage a corresponding fitting of a filling head or nozzle, which may contain a medication supply tube (not shown). In the illustrated embodiment of FIG. 18, outer surface 212 of adapter 210 has a hexagonal shape, but it is also within the scope of the present disclosure for outer surface 212 of adapter 210 to be threaded or otherwise shaped to engage the filling head or nozzle. This open configuration allows medication 102 (FIG. 1) from the supply tube to flow through adapter 210, through the open fill port 130 of port connector 120, and into container 110 (FIGS. 1 and 2).

Figure 21:
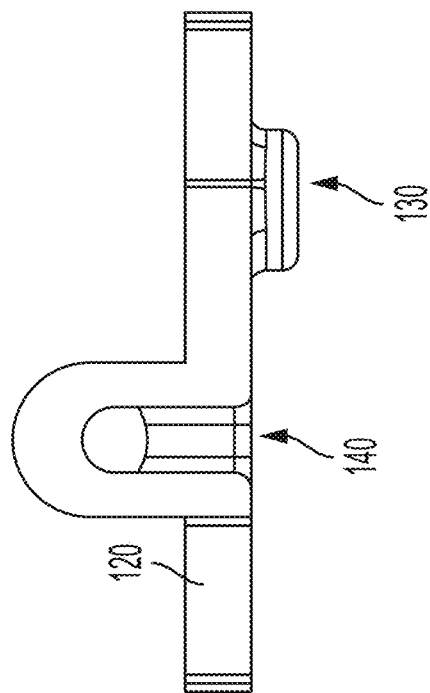
FIG. 21 is a top plan view of the port connector of FIG. 20.
Figure 20:
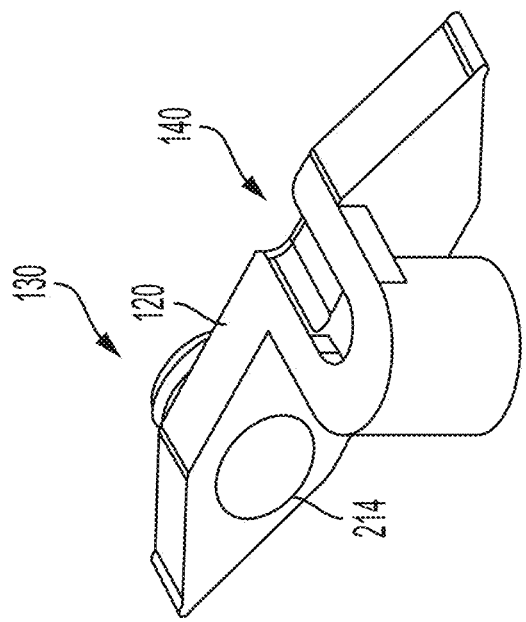
FIG. 20 is a perspective view of the port connector of FIG. 18 with the adapter removed and a plug inserted into the fill port in a sealed configuration.
Figure 23A:
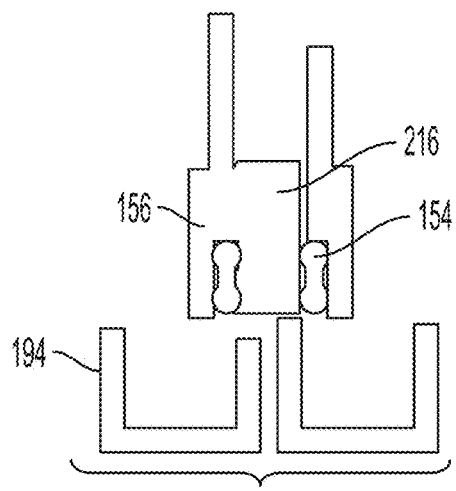
FIGS. 23A-23D are various embodiments of pins with various embodiments of retention features.
Figure 23B:
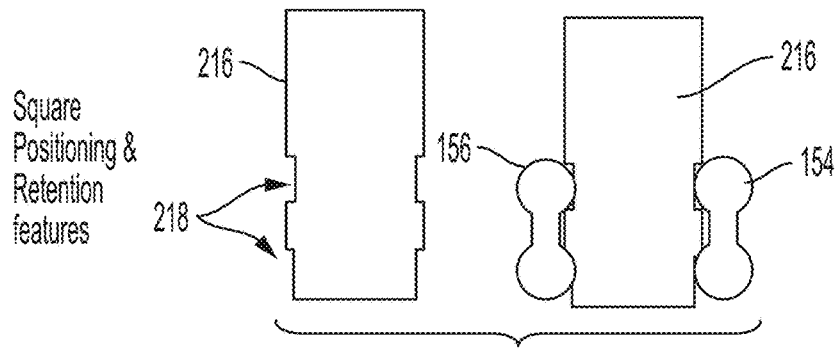
Figure 23C:
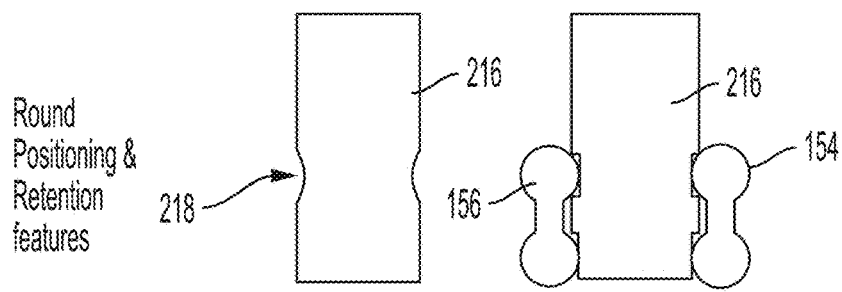
Figure 23D:
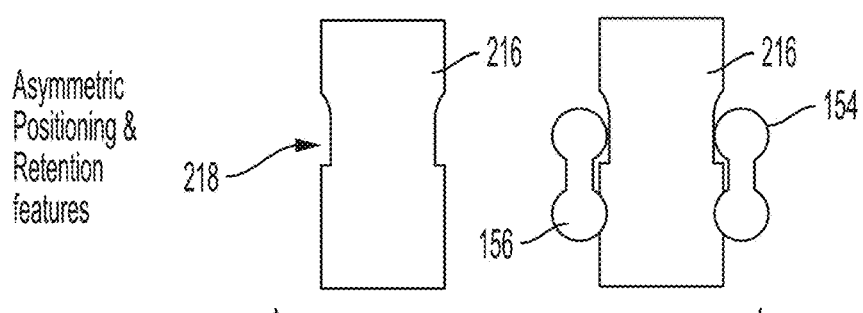
Figure 24B:
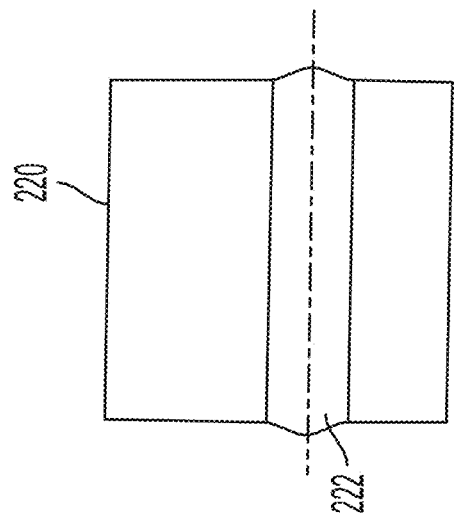
FIGS. 24A-24B are various views of one embodiments of a pin.
Figure 24A:
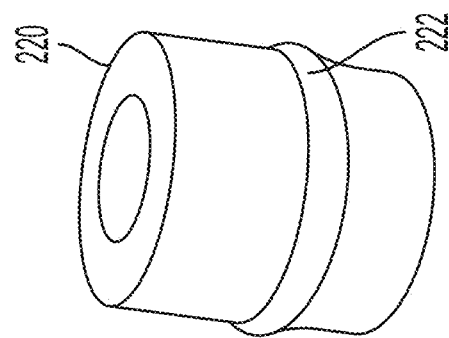
Figure 25B:
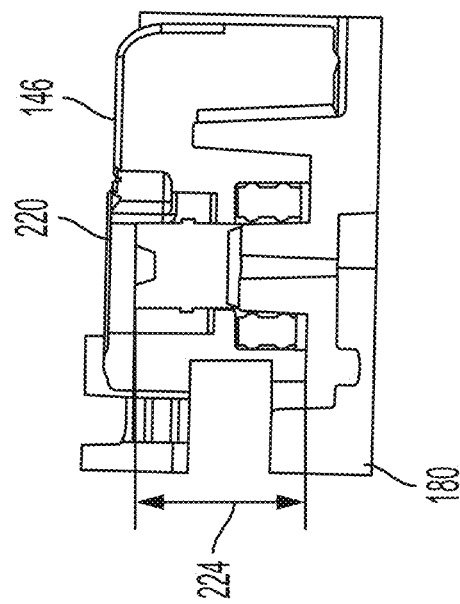
FIGS. 25A-25B show an embodiment of a pin.
Figure 25A:
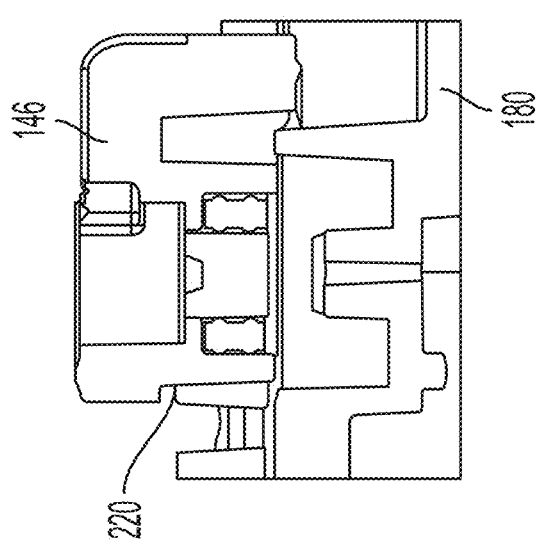

Referring now also to FIGS. 20 and 21 show port connector 120 in a sealed configuration, wherein adapter 210 is removed and replaced with a plug 214 (e.g., a butyl elastomer plug) to close fill port 130 of port connector 120. Adapter 210 may be broken, cut, or otherwise removed from fill port 130 and replaced with plug 214. In the illustrated embodiment, plug 214 is pushed through the central bore of filling adapter 210 and into port 130 immediately following the filling of the container and prior to removing adapter 210 from port connector 120. Adapter 210 may be integrally molded to port connector 120 or alternatively be a separate component that is coupled to port connector 120 prior to filling and handling and then dissembled from port connector 120 after stoppering port 130 with plug 214.

Referring now also to FIGS. 22A-22B, in various embodiments, including in any one or more of the embodiments described and shown herein, a headless pin 216 may be used rather than a pin 150 with a head 151 (see FIG. 3). In various embodiment, it may be desirable/beneficial for the pin 150 to have a head 151 for many reasons, including, but not limited to, the head 151 may serve as a mating hard-stop surface on the delivery port 140 when the pin 151 is inserted into the delivery port 140 during manufacture. In various other embodiments, the shape, size, height, width, etc., of the pin 150 and head 151 may be any shape, size, height, width, etc.

However, in various embodiments, a headless pin 216 may be desirable/beneficial for many reasons, including, but not limited to, the headless pin 216 has smaller radial dimensions than a pin 150 with a head 151 and the delivery port 140 may therefore have smaller dimensions; the headless pin 216 may be smaller in overall length than, for example, a pin 150 with a head 151, thereby the headless pin 216 may allow the delivery port 140 to be shorter; a headless pin 216 is essentially easier to manufacture as, in some embodiments, it may be extruded and cut to length rather than injection molded and this may improve tolerances that may be held on the headless pin 216 and obviates the need for a draft angle on the pin 150 with a head 151; during assembly, the headless pin 216 may be inserted into the deliver port 140 from either side of the delivery port 216; the cross-sectional area of the headless pin 216 may be minimized and therefore the pressure difference on either side of the headless pin 216 results in a smaller force, relative to a pin 150 with a head 151, which has a larger cross sectional area and therefore, the headless pin 216 is less likely to move when the delivery port 140 is pressurized; and the headless pin 216 may have additional features, including, but not limited to, indentations that may be used to aid in position and retention of the headless pin 216 in the delivery port 140 (see FIGS. 23A-23D).

Referring now also to FIGS. 23A-23D, the pin 216 may be fabricated with positioning and retention features 218 that engage the seal 154, 156 at defined positions in the various embodiments. In various embodiments, the positioning and retention features 218 may be any shape and/or size and there may be more than one, depending on one or more considerations, including the seal shape and size. For example, the positioning and retention features 218 may be oval in shape (see FIG. 23A), wherein this shape may be beneficial/desirable for many reasons, including but not limited to, the seals 154, 156 mate with the retention feature 218, thereby helping to locate the pin 216, and preventing it from moving. Still referring to FIGS. 23A-23D, in some embodiments, there may be more than one retention feature 218 (see FIGS. 23A-23B, for example), and, in other embodiments, there may be a single retention feature 218 (see, for example, FIGS. 23C and 23D). The retention feature 218 may be any size or shape desirable, for example, in some embodiments, the shape may be round or oval (see FIG. 23C), and in other embodiments, the shape may be asymmetric and/or square (see FIGS. 23B and 23D). The retention feature 218 retains the pin 216, in some embodiments, in one direction, while allowing it to slip more easily in the other direction. In various embodiments, the retention feature 218 may be shaped and or sized differently than shown and in various embodiments, there may be more than one and/or more than two retention features 218.

Referring now also to FIGS. 24A-25B, another embodiment of a pin 220 is shown. In various embodiments, the pin 220 may include a bead 222. In various embodiments, the bead 222 helps maintain the location of the pin 220 during transit and may reduce displacement of the pin 220 during manufacture. In various embodiments, the pin 220 may be manufactured as a cut extruded rod. In various embodiments, this embodiment of the pin 220 may make the total height 224 lower than other embodiments.

Figure 26A:
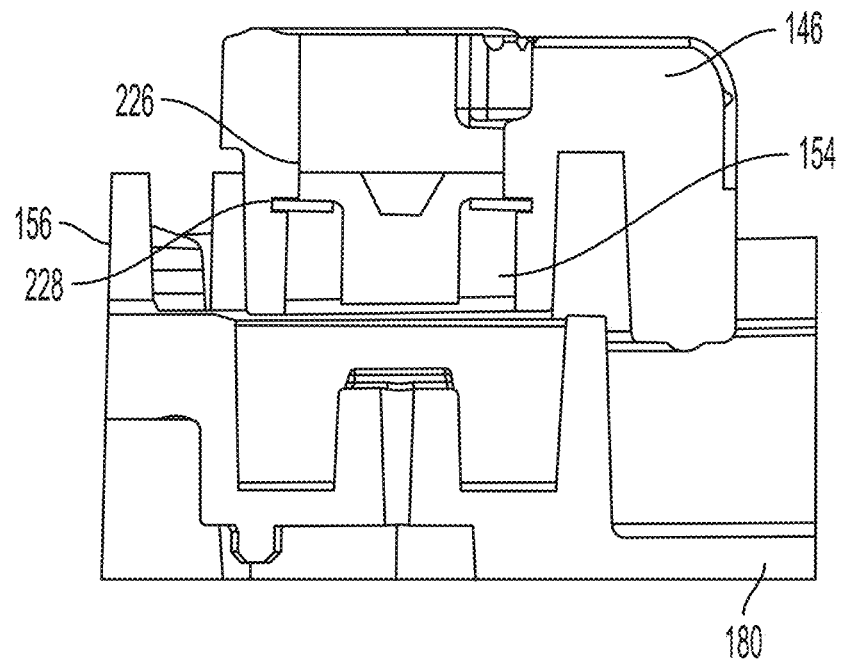
FIGS. 26A-26B show an embodiment of a pin with a shim feature.
Figure 26B:
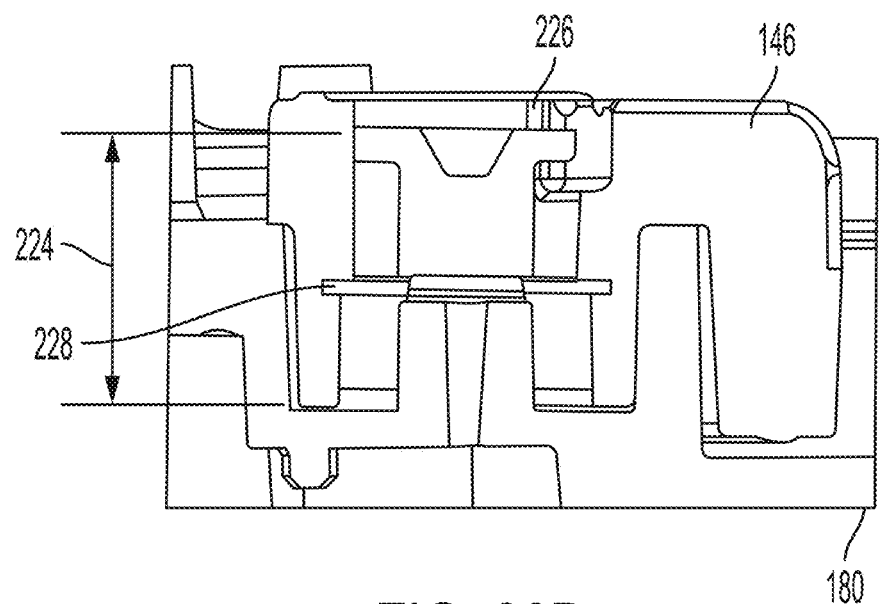

Referring now also to FIGS. 26A-26B, another embodiment of the pin 226 is shown. In some embodiments, a shim 228 may be used to reduce the length of the pin 226. In various embodiments, this embodiment of the pin 226 may make the total height 224 lower than other embodiments.

Figure 27A:
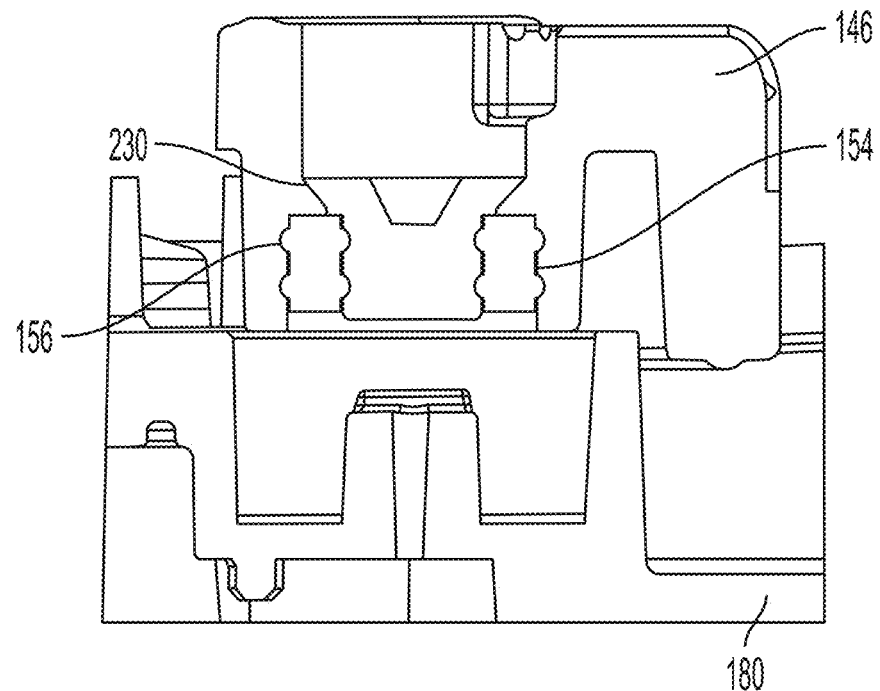
FIGS. 27A-27B show one embodiment of a pin.
Figure 27B:
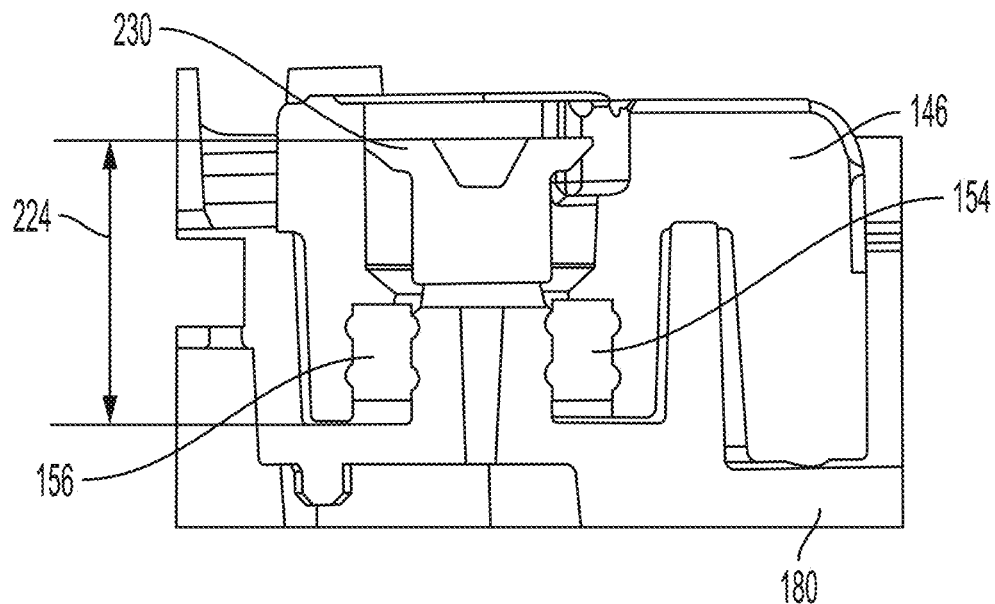

Referring now also to FIGS. 27A and 27B, in various embodiments, features of the pin 230 may be overlapped by using a conical surface and therefore, the pin 230 nests into a cone geometry and saves total height 224. In various embodiments, this embodiment of the pin 220 may make the total height 224 lower than some other embodiments.

Figure 28:
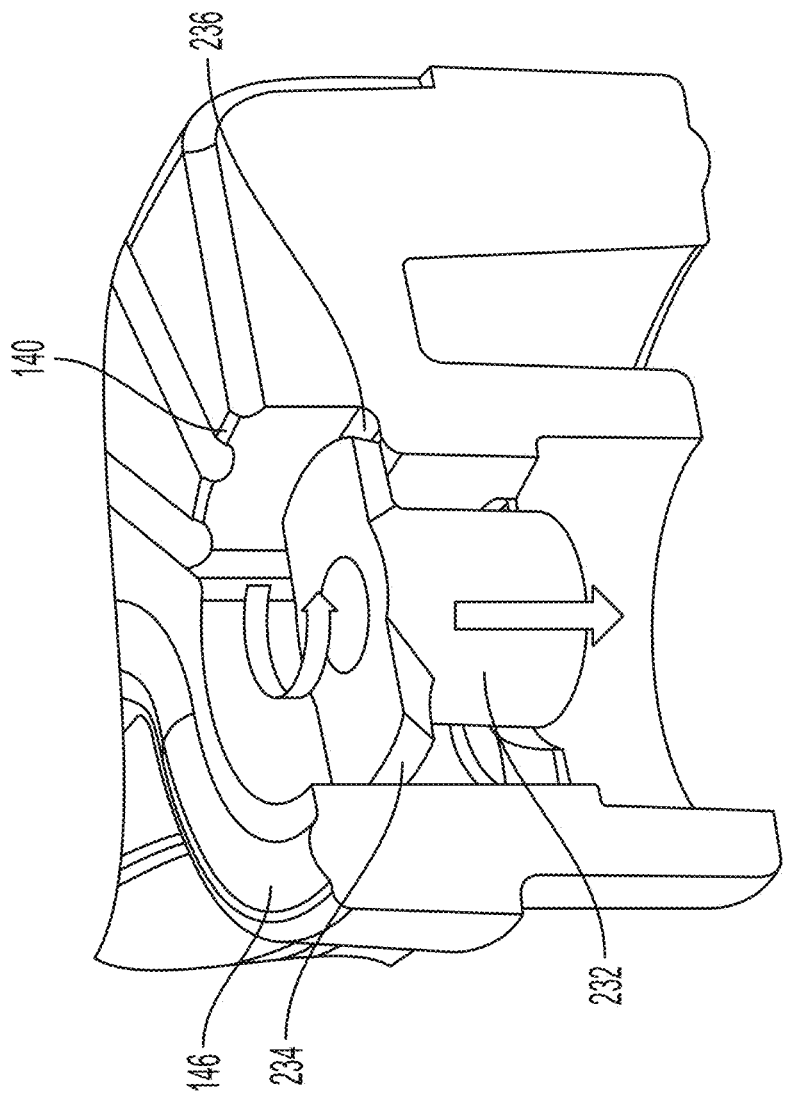
FIGS. 28-29B are various views of one embodiment of a pin.
Figure 29B:
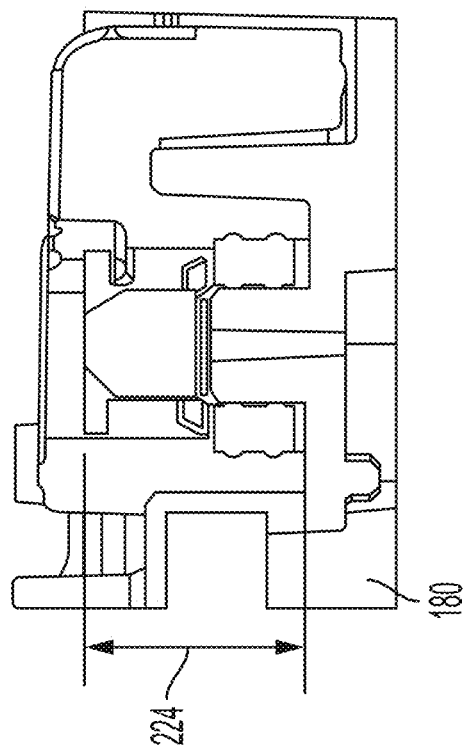
Figure 29A:
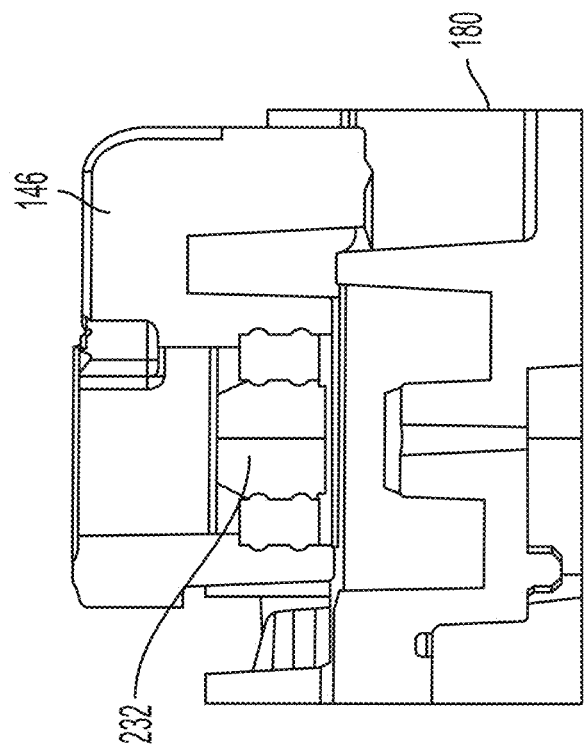

Referring now also to FIGS. 28-29B, in various embodiments, the pin 232 has wing features 234, which are retained by angled surfaces 236 in the retaining ring of the port 140. In various embodiments, the pin 232 is rotated as the connector is assembled. In various embodiments, rotating the pin 232 as the connector is assembled may overcome 'spring back' of the pin 232. Single feature datums both seal and pin saving a wall thickness of material. In various embodiments, this embodiment of the pin 232 may make the total height 224 lower than other embodiments.

Figure 30B:
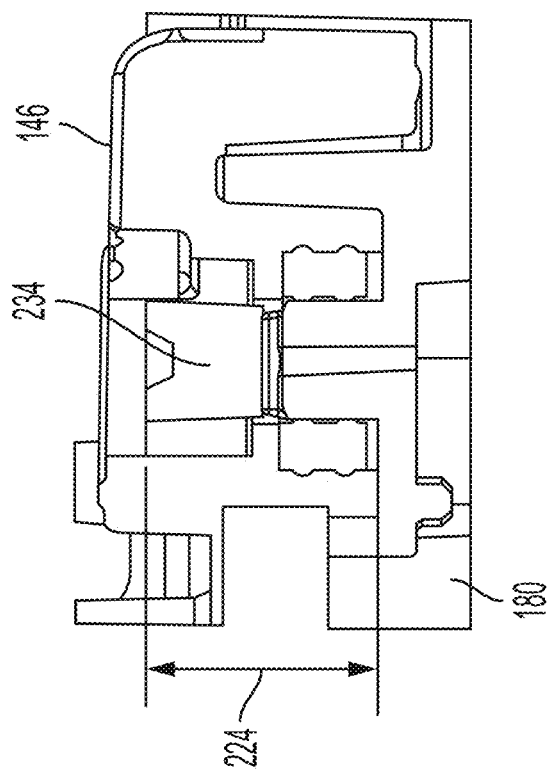
FIGS. 30A-30B show one embodiment of a pin.
Figure 30A:
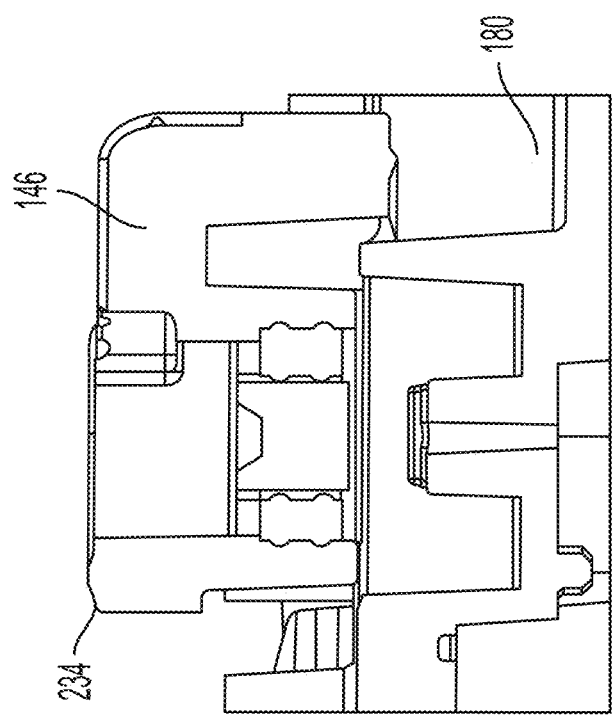

Referring now also to FIGS. 30A-30B, in various embodiments, the pin 234 may not include a flange or wing, and in various embodiments, this may decrease the size of the pin 234. In various embodiments, this embodiment of the pin 234 may make the total height 224 lower than other embodiments.

Figure 31:
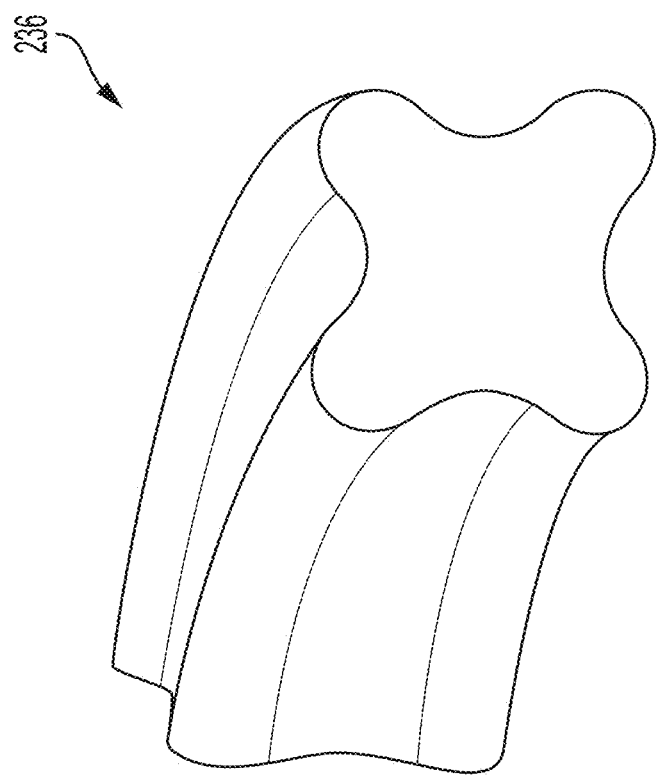
FIG. 31 shows one embodiment of a seal.

Referring now also to FIG. 31, in some embodiments, the shape and size of the seals may vary. In some embodiments, the seal 236 may include a quad-ring geometry. In some embodiments, the aspect ratio of a quad-ring geometry seal 236 may provide a more compact design, leading to a seal 236 that has minimal depth. In various embodiments of the device using a quad-ring seal 236, the retention features 218 may vary to accommodate the different shape of the quad-ring seal 236.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A delivery port for use with a delivery device, the delivery port comprising: an inlet; an outlet; a pin having a shoulder; a first seal positioned about said pin adjacent said shoulder, said shoulder transferring movement of a port connector to the first seal; and a second seal positioned about said pin adjacent and on the same side of said shoulder, said shoulder transferring movement of the port connector to the second seal, wherein the port connector having a sealed configuration in which the first and second seals are positioned in sealed engagement with the pin to close the delivery port; an intermediate configuration in which the first seal is positioned in sealed engagement with the delivery device and the second seal is positioned in sealed engagement with the pin; and a delivery configuration in which the first seal is positioned in sealed engagement with the delivery device and the delivery port is positioned in fluid communication with a fluid passageway of the delivery device.

2. The delivery port of claim 1, wherein in the delivery configuration, the first and second seals are positioned in sealed engagement with the delivery device.

3. The delivery port of claim 1, wherein in the delivery configuration, the first seal is positioned in sealed engagement with the delivery device and the second seal is positioned in sealed engagement with the pin.

4. The delivery port of claim 1, wherein the first seal is positioned below the shoulder and the second seal is positioned above the shoulder.

5. The delivery port of claim 1, wherein the port connector includes a fill port configured to transfer fluid from an external source.

6. The delivery port of claim 5, wherein the delivery port is positioned along a first axis and the fill port is positioned along a second axis, and the first axis is substantially perpendicular to the second axis.

* * * * *